United States Patent
DeArmond

(10) Patent No.: US 9,955,896 B2
(45) Date of Patent: May 1, 2018

(54) PROTECTIVE MATRIX FOR INTRACORPOREAL BIOSENSORS THAT IMPROVES GASTROINTESTINAL LEAK DETECTION, DETECTS AIR LEAKS AFTER LUNG SURGERY, AND MEASURES CARDIAC OUTPUT AFTER HEART SURGERY

(71) Applicant: Daniel T. DeArmond, San Antonio, TX (US)

(72) Inventor: Daniel T. DeArmond, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 677 days.

(21) Appl. No.: 13/934,914

(22) Filed: Jul. 3, 2013

(65) Prior Publication Data
US 2014/0018696 A1   Jan. 16, 2014

Related U.S. Application Data

(60) Provisional application No. 61/667,715, filed on Jul. 3, 2012.

(51) Int. Cl.
*A61B 5/053* (2006.01)

(52) U.S. Cl.
CPC .................. *A61B 5/0538* (2013.01)

(58) Field of Classification Search
CPC ........................... A61B 5/05–5/0538
USPC ...................................................... 607/139
See application file for complete search history.

(56) References Cited

U.S. PATENT DOCUMENTS

| | | | |
|---|---|---|---|
| 2,308,933 A * | 1/1943 | Raesler | A61B 5/0531 600/547 |
| 4,406,878 A | 9/1983 | Deboer | |
| 4,697,593 A | 10/1987 | Evans et al. | |
| 5,357,956 A | 10/1994 | Nardella | |
| 5,749,369 A | 5/1998 | Rabinovich et al. | |
| 5,828,184 A | 10/1998 | Nadd | |
| 5,916,171 A | 6/1999 | Mayevsky | |
| 6,032,077 A * | 2/2000 | Pomeranz | A61B 17/00234 606/41 |

(Continued)

OTHER PUBLICATIONS

Bruce et al. "Systematic review of the definition and measurement of anastomotic leak after gastrointestinal surgery," British Journal of Surgery, 2001, vol. 88, pp. 1157-1168.

Heiken et al., "CT Evaluation after Esophagogastrectomy," American Journal of Roentgenology (AJR), 1984, vol. 143, pp. 555-560. (Abstract).

(Continued)

*Primary Examiner* — David J McCrosky
(74) *Attorney, Agent, or Firm* — Meyertons, Hood, Kivlin, Kowert & Goetzel, P.C.

(57) ABSTRACT

The system and method may measure and monitor physiological changes in a body. In some embodiments, the system and method may measure the impedance at a site in the body. In some embodiments, the system and method identify, quantify, and localize leaks from a site following surgery, measure cardiac contractility, or lung compliance. In an embodiment, the system includes a measuring device with one or more sensors embedded in a porous matrix. Changes in the electrical properties of one or more sensors may be used to determine the presence of leaks from a site following surgery, measure cardiac contractility, or lung compliance, depending on the position of the device.

12 Claims, 33 Drawing Sheets

(56) References Cited

U.S. PATENT DOCUMENTS

| | | | |
|---|---|---|---|
| 6,112,123 A * | 8/2000 | Kelleher | A61B 18/1206 606/27 |
| 6,360,123 B1 | 3/2002 | Kimchi et al. | |
| 6,425,877 B1 | 7/2002 | Edwards | |
| 6,512,949 B1 | 1/2003 | Combs et al. | |
| 7,245,954 B2 | 7/2007 | Glukhovsky | |
| 2003/0216663 A1 | 11/2003 | Jersey-Willuhn et al. | |
| 2004/0133079 A1 | 7/2004 | Mazar et al. | |
| 2004/0254432 A1 | 12/2004 | Necola Shehada et al. | |
| 2005/0124908 A1 | 6/2005 | Belalcazar | |
| 2005/0240093 A1 * | 10/2005 | DeArmond | A61B 5/02042 600/372 |
| 2009/0118662 A1 * | 5/2009 | Schnall | A61M 37/0015 604/20 |
| 2012/0143020 A1 * | 6/2012 | Bordoley | A61B 5/1114 600/383 |

OTHER PUBLICATIONS

Herrlin, K., "The Diagnosis of Anastomotic Leak After Gastroesophagostomy with Biliary Scintigraphy," Clinical Nuclear Medicine, 1995, vol. 20, pp. 709-711. (Abstract).

Junger et al., "Early detection of anastomotic leaks after colorectal surgery by measuring endotoxin in the drainage fluid," Hepatogastroenterology, 1996, abstract as displayed from PubMed; 1 page. (Abstract).

Marshall et al, "Roux-en-Y Gastric Bypass Leak Complications," Archives of Surgery, 2003, vol. 138, pp. 520-524. (American Meidacl Association). (Abstract).

Ovnat et al., "Early Detection and Treatment of a Leaking Gastrojejunostomy Following Gastric Bypass," Israel Journal by Mecial Sciences, 1986, vol. 22, pp. 556-558 (Abstract).

Sing et al, "Sensitivity and specificity of postoperative upper GI series following gastric bypass," Obesity Surgery, 2003, abstract as displayed from PubMed; 1 page (Abstract).

* cited by examiner

PROTECTIVE MATRIX FOR INTRACORPOREAL BIOSENSORS THAT IMPROVES GASTROINTESTINAL LEAK DETECTION, DETECTS AIR LEAKS AFTER LUNG SURGERY, AND MEASURES CARDIAC OUTPUT AFTER HEART SURGERY

PRIORITY CLAIM

This application claims the benefit of U.S. Provisional Application No. 61/667,715 filed on Jul. 3, 2012.

BACKGROUND OF THE INVENTION

1. Field of the Invention

The present invention relates to systems and methods for measuring and monitoring physiological changes in a body.

2. Description of the Relevant Art

Surgery involving the gastrointestinal tract is commonly performed for a variety of reasons. In many cases, gastrointestinal surgery involves the division of the gastrointestinal tract and removal of a segment of the gastrointestinal tract. When the gastrointestinal tract is divided and/or a segment of the gastrointestinal tract is removed, a subsequent re-connection is performed to restore gastrointestinal continuity using suture material, surgical stapling devices, and/or various reinforcing materials. This re-connection is referred to as a gastrointestinal anastomosis.

Anastomotic leak is a potentially devastating complication of esophagectomy that occurs in 3-25% of cases and results in mortality as high as 20-50%. Early diagnosis is critical to minimizing morbidity and mortality and for this reason it remains common practice to perform routine upper gastrointestinal (GI) contrast fluoroscopy after surgery to identify leaks before they present clinically. However, numerous studies have questioned the value of routine post-esophagectomy upper GI contrast fluoroscopy because of its low sensitivity in identifying anastomotic leak. In a prospective trial examining fluoroscopy using a water soluble contrast agent, the sensitivity for detection of an anastomotic leak was reported as only 40%. The addition of high-density barium may increase the sensitivity of upper GI fluoroscopy by 60%. Computed tomography scanning with aqueous enteral contrast has been proposed as an alternative to upper GI fluoroscopy but its utility may also be limited; one prospective study showed a sensitivity of only 73% for anastomotic leak for CT with enteral contrast. Upper gastrointestinal endoscopy has a reported sensitivity and specificity for anastomotic leak of 100% but since it requires an invasive procedure it is unlikely to be adopted as a routine post-operative diagnostic modality in all patients. Because of the lack of a sensitive, non-invasive study to identify anastomotic leak in post-esophagectomy patients, a significant number of leaks are not detected until they present clinically.

In summary, anastomotic leak is a major source of morbidity and mortality after upper gastrointestinal surgery that is most effectively treated when it is recognized early. However, no definitive diagnostic test for anastomotic leak exists at the current time and the sensitivity and specificity of the methods currently used have not been adequately determined. Moreover, in the medical literature, authors have pointed to the need for better definition of and identification of anastomotic leaks to improve the care of patients who undergo gastrointestinal surgery. Therefore, there is a recognized need for a device that would provide improved anastomotic leak detection.

SUMMARY OF THE INVENTION

In an embodiment, a physiological change monitoring system includes: a porous matrix, wherein the porous matrix is configured to be positionable in an opening in a body during use; one or more sensors disposed in the porous matrix, wherein at least one sensor is configured to measure physiological changes in the opening in the body; and a measurement determining unit coupled to the one or more sensors, wherein the measurement determining unit is configured to determine a change in the electrical properties of the one or more sensors. In an embodiment, the electrical properties measured include an impedance associated with the one or more sensors.

In an embodiment the porous matrix is positionable proximate an organ, wherein at least one sensor directly measures physiological changes. A biologically inert liquid may be absorbed in the porous matrix. In an embodiment, the porous matrix is positioned in a container. A biologically inert liquid, absorbed by the porous matrix, may leave the porous matrix during compression of the porous matrix contained by the container. The container may contain the biologically inert liquid to prevent loss of the liquid into the subject body. In an embodiment, a balloon is positioned in the container, wherein inflation of the balloon compresses the porous matrix. The sensors may be positioned in the porous matrix such that the distance between the sensors changes as the porous matrix is compressed or expanded. In another embodiment, the sensors are coupled to a substantially inflexible substrate positioned within the porous matrix, wherein the distance between the sensors does not change when the porous matrix is compressed of expanded.

The porous matrix may have a shape complementary to: a portion of a human esophagus, a portion of a lung; a portion of a gastrointestinal tract; a portion of a stomach; or a portion of a heart. In some embodiments, the porous matrix is substantially flexible and is moldable to the space within the subject that is being monitored.

A method of monitoring physiological changes in a body includes: inserting a monitoring device in an opening of the body, wherein the monitoring device comprises two or more sensors disposed in a porous matrix, and a measurement determining unit coupled to at least one sensor; and monitoring the electrical properties of the one or more sensors proximate the organ using the measurement determining unit.

In one embodiment, the method also includes introducing a fluid into the body; and monitoring the electrical properties of the one or more sensors after fluid is introduced into the body. In another embodiment, a subject a contrast solution is introduced into a subject. The contrast solution is allowed to flow through the body. One or more leaks may be detected using one or more of the sensor if the monitoring device detects contrast fluid contacting one or more sensors. The contrast solution, in some embodiments, is a saline solution. In some embodiments, the electrical properties measured by one or more sensors are compared to a base line value for a physiological condition. If the electrical properties deviate greater than a selected range from the base line value for the physiological condition, a signal may be created by the physiological change monitoring system to indicate the presence of a leak. The leak may be detected, in an embodiment, by transmitting the impedance to the measurement detection unit; comparing the impedance to a base line value for the impedance; and producing a signal when the impedance deviates greater than a selected range from the base line value.

In an embodiment, the porous matrix is compressible and the method includes placing the porous matrix such that is embedded in or otherwise affixed to the interior or exterior of a heart and monitoring the electrical properties of the one or more sensors proximate the heart using the measurement determining unit, wherein changes in the electrical properties of the sensors are used to determine the cardiac contractility of the heart. One or more of the sensors may be capable of determining the presence of blood in the porous matrix.

In an embodiment, the porous matrix is compressible and the method includes placing the porous matrix such that it is embedded in or otherwise affixed to the interior or exterior of a lung and monitoring the electrical properties of the one or more sensors proximate the lung using the measurement determining unit, wherein changes in the electrical properties of the sensors are used to determine the compliance of the lung.

In an embodiment, the porous matrix is compressible and the method includes placing a porous matrix in contact with tissue and monitoring the electrical properties of the one or more sensors proximate the tissue using the measurement determining unit, wherein changes in the electrical properties of the sensors are used to determine the mechanical resistance of the tissue.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
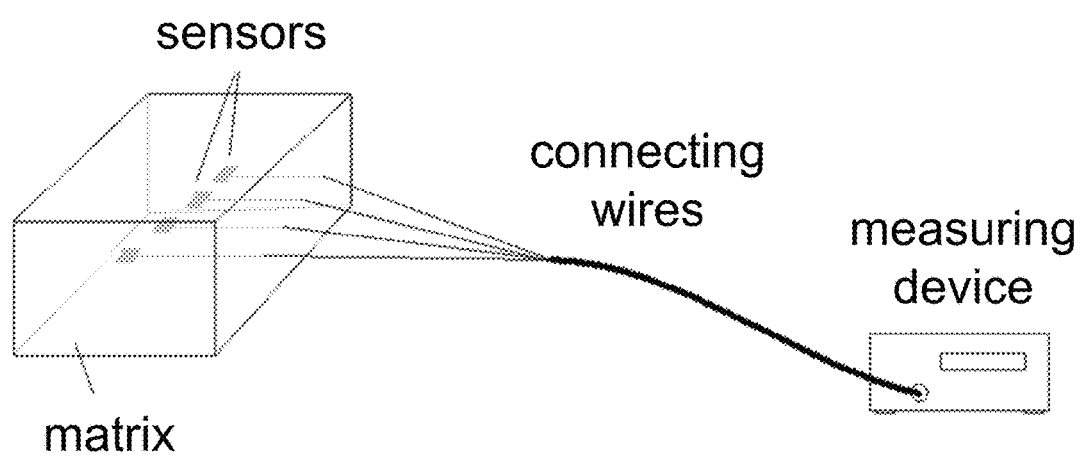
FIG. 1 depicts a schematic diagram of electrical resistance-detecting electrodes in a porous matrix housing.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Organs and tissue in a human body possess an ability to conduct electricity due to their biological structures. A body is composed of cells, fluid, and/or air compartments that include a mixture of electrically conductive and resistive elements. The mixture of conductive and resistive elements determines the electrical properties of a given portion of a body. Impedance, in the context of this application, refers to the ability to resist electrical currents. Cells, fluid, and/or air spaces all contribute to the electrical impedance that a given organ or tissue exhibits. When physiological changes occur in a body, changes in cells, fluid, and/or air spaces may occur and the electrical impedance of a portion of a body may be measurably altered. Leaking fluid and/or air from a portion of a body also may be detected by a change in impedance.

A physiological change monitoring system may allow precise, minute-by-minute monitoring of changes in a body as manifested by impedance changes. A physiological change monitoring system may allow precise, minute-by-minute monitoring of tissue edema as manifested by tissue impedance.

Herein we describe a system and method for measuring and monitoring physiological changes at a site in the body. In one embodiment, the system and method may measure the impedance at a site in the body. In some embodiments, the system and method may be used to identify and quantify leaks from a site following surgery. In an embodiment, the system includes one or more sensors embedded in a porous matrix. The porous matrix may be at least partially positioned in an opening of a body at a site to be monitored. The porous matrix may be formed from a flexible material that may allow the shape of the porous matrix to be selected to facilitate impedance monitoring and/or detection of leaks at a desired site.

A physiological change monitoring system may be placed in a body to directly measure physiological changes at a desired organ, tissue, and/or site. In an embodiment, the physiological change monitoring system may directly measure impedance at a desired organ, tissue, and/or site. A site may be any portion of the body. The system may be used in lungs, gastrointestinal tract, heart, or proximate other organs. A physiological change monitoring system may include a measurement determining unit configured to analyze, calculate, and/or display an impedance. A physiological change monitoring system may detect leaks or movement of organs proximate to the site where the sensors are disposed. Changes in impedance may indicate changes in physiological conditions.

Porous matrix may be formed from a polymeric foam. Examples of polymeric foams include, but are not limited to polyurethanes, polyolefins (such as polyethylene and polypropylene), polyvinylchlorides, polyesters, poly ethylene vinyl alcohols, polyvinyl alcohols, polycaprolactones, polylactic acids and foamed starch. A polymeric material may be expanded foam, such as expanded polyurethane.

In some embodiments, a biologically inert liquid may be placed in the porous matrix. The biologically inert liquid is a liquid that is similar to the liquid that is found in the portion of the body where the porous matrix will be placed. In some embodiments, the biologically inert liquid is a saline solution.

A physiological change monitoring system may include one or more sensors. Sensors may be embedded in the porous matrix. Sensors may be electrodes configured to monitor impedance and/or detect changes in impedance. If a direct current source is used for monitoring, the sensor may monitor resistance and/or detect changes in resistance. In certain embodiments, sensors may measure values other than impedance/resistance (e.g., pH, oxygen levels, ion concentration, light absorption, etc.) and are connected to a corresponding measurement determining device. In an embodiment, measurement determining unit may include a device capable of measuring impedance/resistance. Sensors may also include other sensors such as: pH sensors; ion concentration sensors; light probes; ion selective field effect transistors; microsensors; metabolite sensors; molecularly-imprinted-polymer-biosensors; photodetectors; detectors of radioactivity; pizoelectric-crystal transmitter/receiver units and/or chemical sensors on silicon chips. Measurement determining units may include, but are not limited to, devices for measuring pH, oxygen levels, ion concentration, light absorption, and/or other receiver units. Monitoring pH in a body may be desirable in vascular surgery, lower extremity surgery, kidney surgery, lung surgery, gastrointestinal surgery, neurosurgery, and/or transplants.

Sensors may be coupled to wires that are completely or partially embedded in the porous matrix. Wires may connect one or more sensors to a measurement determining unit. Sensors may transmit data to a measurement determining unit. A measurement determining unit may produce a signal when the impedance/resistance deviates beyond a pre-selected range. Measurement determining unit may be any device capable of analyzing data from a sensor. A measurement determining unit may include an impedance monitoring unit. In an embodiment, measurement determining unit may include a voltmeter. Alternatively, a measurement determining unit may include an ion detector. Wires may exit a body cavity via retractor conduit and exit the refractor conduit via an opening in the retractor conduit. An opening in the retractor conduit may be at an end, proximate an end, or at any other position along the length of the retractor conduit. In an embodiment, wires may be at least partially embedded in a retractor conduit. Wires may be configured to resist damage from fluids in a body cavity. At least partially embedding wires may diminish damage to the wires due to contact with fluids in a body cavity. In an embodiment, wires may be coated with a corrosion resistant material.

In one embodiment, a method of monitoring physiological changes in a body includes: inserting a monitoring device in an opening, proximate to an organ in the body, wherein the monitoring device comprises two or more sensors disposed in a porous matrix, and a measurement determining unit is coupled to at least one sensor; and monitoring the electrical properties of the one or more sensors proximate the organ using the measurement determining unit.

In an embodiment, the monitoring device may be used to monitor leakages or organ dysfunction associated with heart conditions and/or heart procedures. Examples of heart conditions and procedures which may need monitoring after surgery include, but are not limited to, coronary bypass surgery, heart valve surgery, and heart failure medical ICU admissions. In any of these conditions or procedures, the monitoring devices described herein may be placed in an interior or exterior position of the heart to determine the presence of blood in an anatomic location that normally does not have blood or to monitor heart muscle function or alternatively may be placed in the pleural space in apposition to the lung to monitor for the development of lung edema associated with heart failure or the accumulation of fluids in the pleural space.

In another embodiment, a method of measuring cardiac contractility includes: placing a monitoring device in a body such that the monitoring device is embedded in or otherwise affixed to the interior or exterior of the heart, wherein the monitoring device comprises two or more sensors disposed in a porous matrix, and a measurement determining unit is coupled to at least one sensor; and monitoring the electrical properties of the one or more sensors proximate the heart using the measurement determining unit, wherein changes in the electrical properties of the sensors are used to determine the cardiac contractility of the heart.

In another embodiment a method of measuring lung compliance includes placing a monitoring device in a body such that the monitoring device is embedded in or otherwise affixed to the interior or exterior of the lung tissue wherein the monitoring device comprises two or more sensors disposed in a porous matrix, and a measurement determining unit is coupled to at least one sensor; and monitoring the electrical properties of the one or more sensors proximate the lung using the measurement determining unit, wherein changes in the electrical properties of the sensors are used to determine the compliance of the lung and/or the accumulation of air or fluid including blood or fibrinous material in the pleural space. Lung compliance and lung leakages may be monitored in association with lung surgery, lung injuries caused by chest trauma, burns with inhalation injury, empyema requiring a chest tube, spontaneous pneumothorax requiring a chest tube, and pleural effusion (e.g., from malignancy).

* * *

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A method of leak detection, termed electrolyte-gated leak detection (EGLD), which tracks electrical changes induced by extravasated normal saline in the anatomic space surrounding an anastomosis is described in detail in U.S. Pat. No. 7,899,508, issued Mar. 1, 2011, which is incorporated herein by reference. This technique employs electrical resistance-measuring electrodes that could potentially be housed in a surgical drain placed in anatomic proximity to an anastomotic site at the time of surgery. This method of leak detection demonstrated a high degree of sensitivity and specificity in a rat model of anastomotic leak and for this reason we sought to compare EGLD to upper GI fluoroscopy to determine whether EGLD could serve as a viable routine post-operative diagnostic modality for the identification of anastomotic leak. Several reports have shown that enteral contrast solutions of 60-250% weight/volume (w/v) of barium sulfate detect leaks with greater sensitivity than water soluble contrast solutions; for this reason, undiluted barium was chosen as the radiographic contrast solution for the present study.

Materials and Methods
Animals.

Brown Norway rats were obtained from Harlan Laboratories (Indianapolis, Ind.). This study was approved by the Institutional Animal Care and Use Committee of the University of Texas Health Science Center at San Antonio protocol #081 04-35-01-B1.

Rat Model of Gastrointestinal Leak

Rats were anesthetized with inhaled isofluorane (Abbott Laboratories, North Chicago, Ill.). After induction of general anesthesia, an anterior cervical incision was performed through which a tracheostomy was created with a 14-gauge angiocatheter, and an 18-gauge angiocatheter was placed into the cervical esophagus to serve as a gavage catheter for delivery of barium suspension or saline. A small animal ventilator (Harvard Apparatus, Holliston, Mass.) was used to maintain oxygenation and general anesthesia. Through a midline celiotomy, a 5-mm gastrotomy was created in the greater curvature using an aortic punch (Medtronic, Minneapolis, Minn.) to represent the site of anastomotic leak. Prior to introduction of contrast material for leak trials and controls, the stomach was irrigated using saline delivered via the gavage catheter to empty the stomach of all contents. For electrical resistance measurements, the resistance-measuring electrodes were placed in proximity to the leak site with connecting wires brought out of the abdomen through a stab incision positioned lateral to the celiotomy. The celiotomy was then closed and experimental measurements were carried out. For negative controls, a gastrotomy was created then oversewn with 4-0 Vicryl suture.

Electrical Resistance Measurement

A Quantum-II Desktop bioimpedance device (RJL Systems, Clinton Township, Mich.) was used for electrical resistance measurements after zeroing and calibration with a 500-ohm standard resistor. Dynamic resistance was measured to the nearest 0.1 ohms. FIG. 1 depicts a schematic of electrical resistance-detecting electrodes in a porous matrix housing. Saline is added directly to the porous matrix to decrease the baseline electrical resistance or removed from the porous matrix to increase the baseline electrical resistance. Because of previous experience where we noted widely varying baseline resistance measurements within the peritoneum as well as artifacts due to air pockets in the peritoneum and omental entanglement with the resistance-detecting electrodes, the electrodes for this experiment were housed in a sandwich of polyurethane foam (3M, St. Paul, Minn.) bonded with silicone sealant (General Electric, Huntersville, N.C.). The foam sandwich was partially saturated with saline, which allowed it to serve as a matrix for the establishment of a stable baseline resistance for the electrodes. Addition of saline to the foam lowered the baseline resistance sensed by the electrodes; removal of saline from the foam using a suction catheter connected to wall suction raised the baseline resistance. Adjustment of the baseline resistance occurred with the celiotomy still open. After the target baseline resistance value was established, the celiotomy was closed as described above and electrical resistance measurements proceeded. Resistance measurements in both experimental and control animals were initiated to verify the baseline resistance value then continued during the administration of 1 cc of 0.9% normal saline (B. Braun, Irvine, Calif.) via the gavage catheter. Resistance measurements were obtained once per second for 60 seconds. In the electrical resistance measurement portion of the experiment we were able to complete more than one experimental run per animal by re-opening the celiotomy and evacuating extravasated saline then re-establishing the target baseline resistance of the porous matrix surrounding the resistance-measuring electrodes. Experimental animals served as their own negative controls after reopening of the celiotomy and suture-closure of the gastrotomy with 4-0 vicryl suture followed by reclosure of the celiotomy and repeat resistance measurement with the administration of electrolyte in a manner identical to that described above.

Barium Upper GI Fluoroscopy

Anesthetized animals underwent gastrotomy creation as described above. Fluoroscopy was initiated using a portable fluoroscopy device (Siemens, Munich, Germany); 1 cc of undiluted Liquid E-Z-Paque 60% w/v barium sulfate suspension (E-Z-EM Inc., Westbury, N.Y.) was then introduced via the gavage catheter. Fluoroscopy imaging was continued for one minute in an anterior/posterior orientation; no oblique or lateral images were obtained. Cineradiography was recorded on DVD-R discs. It was not possible to carry out fluoroscopic assessment of leak more than once per experimental animal or to have experimental animals serve as their own negative controls due to the inability to evacuate barium completely from the radiographic field. Cineradiography files were interpreted by a radiologist blinded to the experimental procedures to determine the presence or absence of radiographic evidence of leak.

Results

Figure 2:
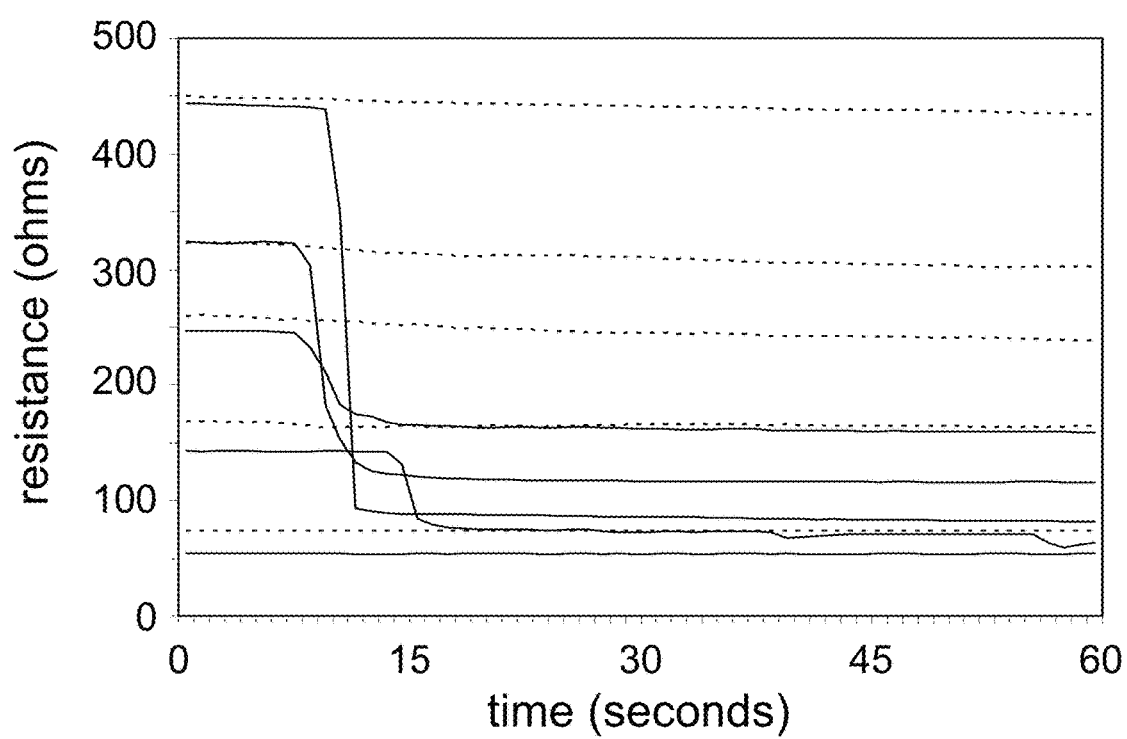
FIG. 2 depicts leak-induced resistance change for different baseline resistance values.
Figure 3:
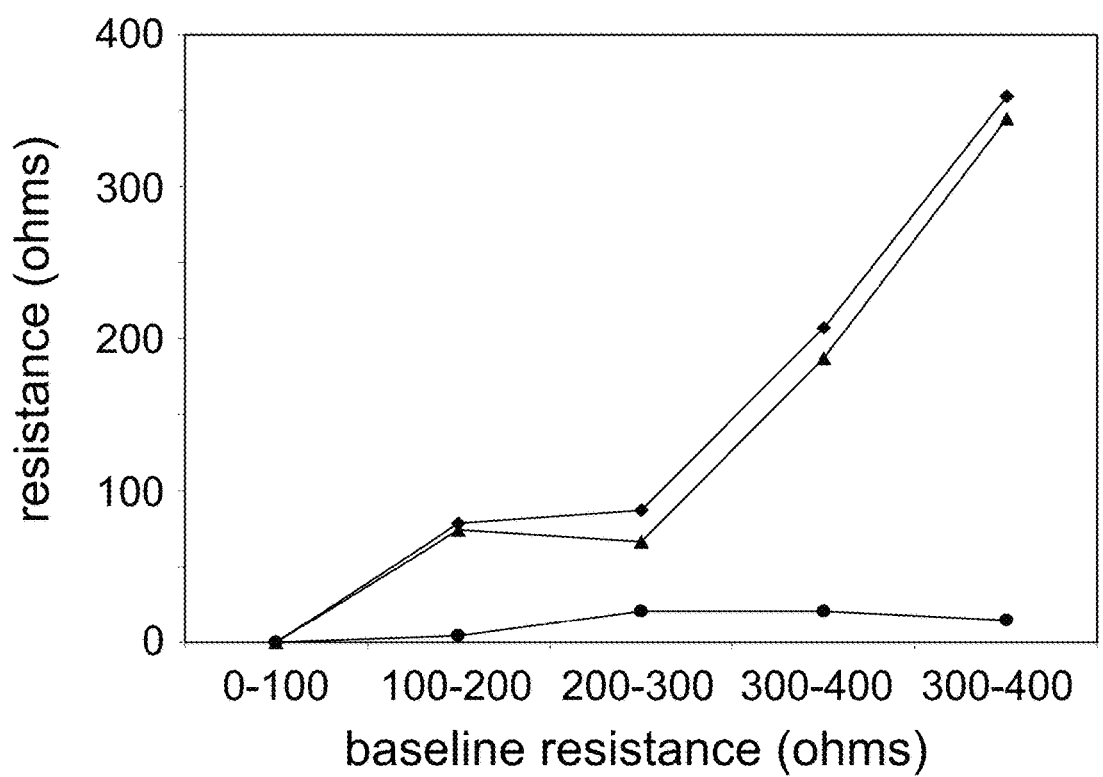
FIG. 3 depicts maximum resistance changes for different baseline resistance values.

Leak-induced resistance change for different baseline resistance values. We sought to identify a baseline resistance value that would allow for a maximization of the difference in measured resistance change between leak runs and controls as a means of improving the signal-to-noise ratio of leak detection by EGLD. By modulating the saline-saturation of the porous matrix that housed the electrodes, the baseline resistance was set to one of five different levels: 0-100 ohms, 100-200 ohms, 200-300 ohms, 300-400 ohms, and 400-500 ohms. Leak measurements and controls were then carried out for each baseline resistance value. By altering the saline-saturation of the porous matrix around the electrodes, the baseline resistance value detected by the electrodes was set to five different ranges: 0-100 ohms, 100-200 ohms, 200-300 ohms, 300-400 ohms, and 400-500 ohms. For each baseline resistance range, a leak run and a control run were performed and measured resistance values over one minute were plotted (leak runs—solid curves; controls—dashed curves). FIG. 3 depicts maximum resistance changes for different baseline resistance values. The maximum resistance change for leak runs (RLmax) and controls (RCmax) and the difference, RLmax-RCmax, were plotted for each baseline resistance range (diamonds—leak runs; circles—controls; difference—triangles) to identify the optimal baseline resistance value for leak detection. When the baseline resistance was set to 0-100 ohms, no difference in the change in resistance after the administration of saline was detectable between the experimental run and control (FIGS. 2 and 3). For all other baseline resistance values, a difference in the change in resistance between experimental and control runs was readily detectable (Table 1, FIGS. 2 and 3). The change in magnitude of the resistance drop for leak runs increased with increasing baseline resistance without an apparent plateau as did the difference between the change in resistance for leak runs versus controls (RL-RC) (FIG. 3). This suggested that the highest signal-to-noise ratio was achieved with the 400-500 ohm baseline and therefore all additional electrical resistance measurements were carried out using this baseline. Baseline resistance values greater than 500 ohms were possible but were time consuming to establish given the limitations of the experimental design. While baseline resistance values greater than 500 ohms were stable once established, it was not possible to attain a specific resistance value in this range with precision due to the fact that very small quantities of saline either added to or removed from the porous matrix entailed large changes in the baseline resistance value (data not shown). For this reason, baseline resistance values greater than 500 ohms were not used in this study.

Figure 4:
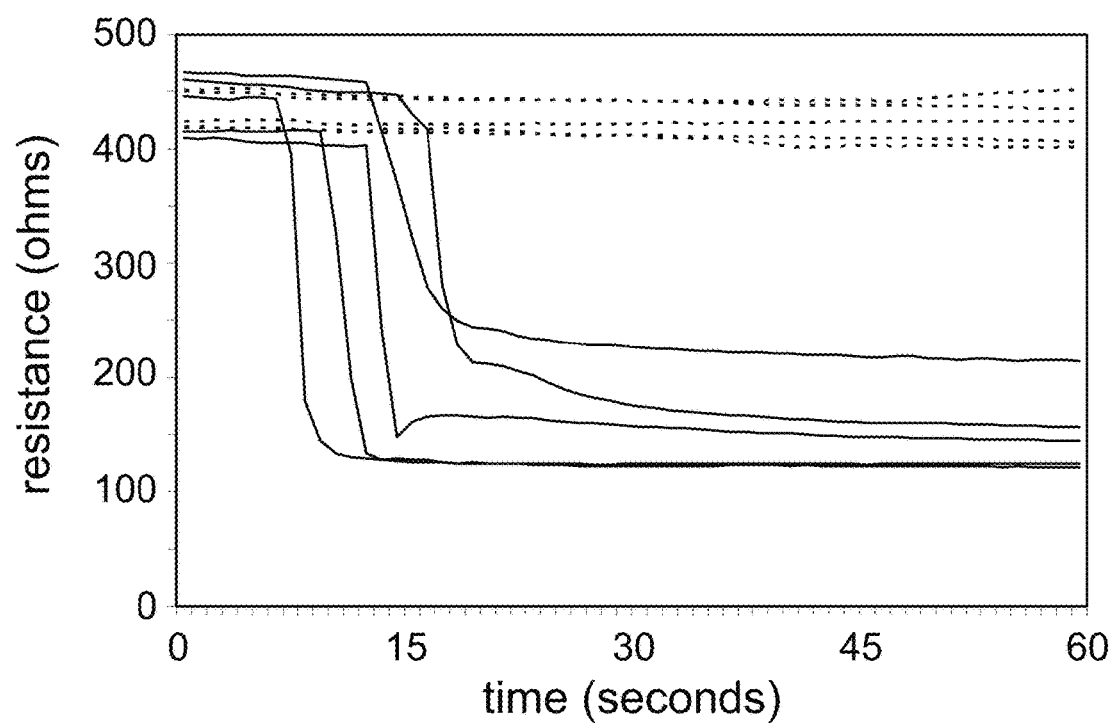
FIG. 4 depicts plots of five consecutive leak runs (solid curves) and controls (dashed curves) starting from a baseline resistance of 400-500 ohms.

Leak detection by EGLD versus barium fluoroscopy. Five consecutive leaks and controls were performed with a resistance baseline set at 400-500 ohms (FIG. 4). There was no significant difference in baseline resistance (Rbaseline) between leak animals and controls (434.7+/−24.3 ohms versus 432.5+/−16.7 ohms, p=0.87). An obvious drop in resistance after the introduction of saline was recorded in all leak animals but not in controls (FIG. 4). The mean maximum resistance drop (Rmax) in the presence of a leak was 282.1+/−29.4 ohms which differed significantly from that for controls (8.9+/−7.4 ohms, p<0.0001) (Table 2). The maximum resistance change in one second ((R/T)max) for leak measurements was also significantly higher than for controls (137.9+/−60.9 ohms/sec versus 1.9+/−1.1 ohms/sec, p=0.0011). The sensitivity and specificity for EGLD detection of leak were both 100% (Table 3).

Figure 5:
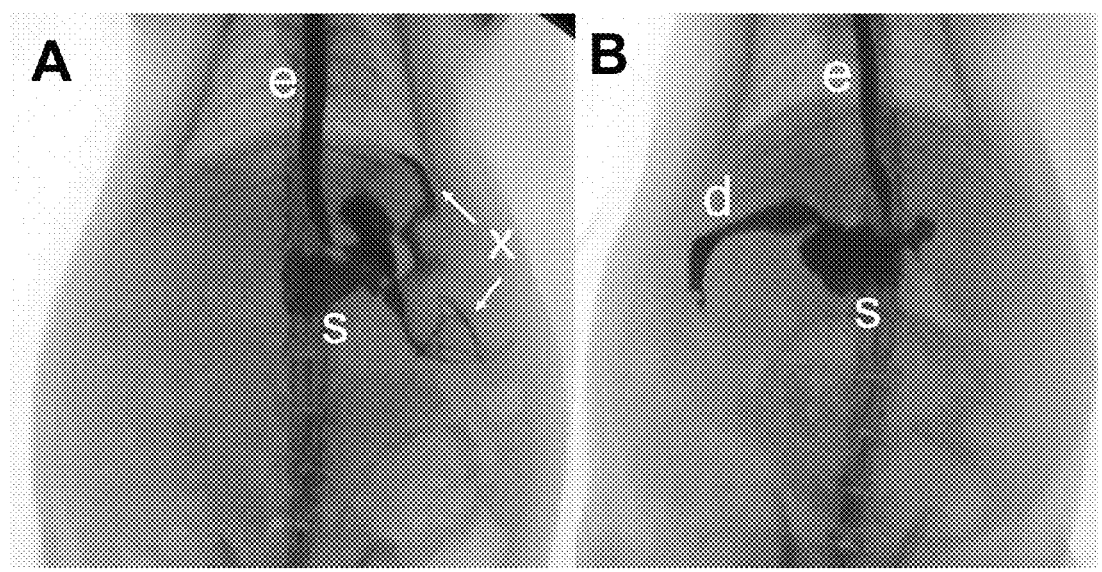
FIG. 5 depicts spot images of barium upper GI fluoroscopy in the rat anastomotic leak model.

FIG. 5 depicts spot images of barium upper GI fluoroscopy in the rat anastomotic leak model. Fluoroscopy was performed on anesthetized rats during the injection of 1 cc undiluted barium into the esophagus via gavage catheter. FIG. 5A in the presence of gastric leak, contrast was seen to flow through the esophagus (e) and into the stomach (s), followed by contrast extravasation (x) into the peritoneum and sub-diaphragmatic recess. FIG. 5B for control animals, the gastrotomy site was suture-closed, preventing extravasation of contrast into the peritoneum. The esophagus (e), stomach (s) and duodenum (d) were contrast enhanced within one minute of contrast introduction. Blinded barium fluoroscopy interpretation by the radiologist misidentified one leak as a control and one control as a leak (Table 3) resulting in a sensitivity and specificity for leak detection of 80% (FIG. 5). There was no statistical difference between the sensitivity or specificity of EGLD versus barium swallow for leak detection (p=0.76).

TABLE 2

Average resistance value and standard deviation for $R_{baseline}$, $R_{max}$, and $(R/T)_{max}$ for leak runs versus controls

|  | Leak runs | Controls |
|---|---|---|
| $R_{baseline}$ (ohms) | 434.7 +/− 24.3 | 432.5 +/− 16.7 |
| p-value versus control | 0.87 | n/a |
| $R_{max}$ (ohms) | 282.1 | 8.9 |
| p-value versus control | <0.0001 | n/a |
| $(R/T)_{max}$ (ohms/sec) | 137.9 +/− 60.9 | 1.9 +/− 1.1 |
| p-value versus control | 0.001 | n/a |

TABLE 3

Sensitivity and specificity for anastomotic leak detection by EGLD and barium upper GI fluoroscopy

|  | EGLD | | barium upper GI fluoroscopy | |
|---|---|---|---|---|
|  | leak identified | leak not identified | leak identified | leak not identified |
| leak present | 5 | 0 | 4 | 1 |
| leak not present | 0 | 5 | 1 | 4 |

Articles debating the ideal modality for the detection of anastomotic leak after esophagectomy suggest that the issue is not fully resolved for clinicians who diagnose and treat this condition. While upper GI contrast fluoroscopy has been used for several decades in this capacity, limitations with respect to sensitivity as well as persistent concerns about

TABLE 1

Resistance change for leak runs and controls by baseline resistance value

| Baseline resistance value (ohms) | Resistance change for leak runs ($R_L$) (ohms) | Resistance change for controls ($R_C$) (ohms) | $R_L - R_C$ (ohms) |
|---|---|---|---|
| 0-100 | 0.03 | 0.2 | 0.1 |
| 100-200 | 78.4 | 4.2 | 74.2 |
| 200-300 | 87 | 20.6 | 66.4 |
| 300-400 | 207.2 | 20.5 | 186.7 |
| 400-500 | 359.3 | 14.7 | 212.3 | adverse reactions associated with enteral contrast agents stimulate authors to look for alternative diagnostic modalities for anastomotic leak.

The primary purpose of the current study was to compare the sensitivity and specificity of EGLD to upper GI contrast fluoroscopy for the diagnosis of anastomotic leak. Power analysis determined that approximately 45 animals per experimental arm would have been required to achieve statistical significance. We found that the sensitivity and specificity of EGLD for anastomotic leak was not less than that of upper GI fluoroscopy, suggesting that EGLD may be useful as a routine diagnostic method of anastomotic leak detection after esophagectomy. Importantly, there may be several distinct advantages of EGLD over upper GI fluoroscopy. First, the saline contrast agent is inert and does not present a risk if extravasation occurs. Secondly, leak assessment theoretically could be conducted at the bedside eliminating the need to transport the patient to radiology. Finally, real-time continuous surveillance for anastomotic leaks may be accomplished using EGLD.

The manner in which we carried out upper GI fluoroscopy in this study was atypical and may represent a limitation of this study. Upper GI fluoroscopy in humans does not set a strict limit on the volume of contrast material used and may include oblique or lateral views. In our study, the volume of barium used was limited to 1 cc per animal and fluoroscopy was only performed in an anterior/posterior orientation. These restrictions represented an attempt to equalize the conditions under which the sensitivity of barium versus saline as a contrast agent was examined. As we showed in the present study (FIG. 4) only 1 cc of saline was required to identify anastomotic leak with a high degree of sensitivity and specificity almost instantaneously upon saline gavage without the need for repositioning of experimental animals or of moving any portion of the leak-detecting equipment. However, the performance of oblique or cross-table lateral views might have improved sensitivity in the fluoroscopy cohort.

A secondary purpose of this study was to investigate further refinements of EGLD. In our previous study, baseline resistance values obtained from within the peritoneum demonstrated marked variability resulting in a large standard deviation for the resistance change induced by extravasated saline. We attributed this variability to inconsistencies in the electrode-to-patient interface that can lead to error in bioimpedance measurements as noted in previous studies. While the maximum resistance change ($R_{max}$) of leak runs was nonetheless significantly different from that of controls in our previous study, an examination of the maximum slope of resistance change, $(R/T)_{max}$, failed to reveal a statistically significant difference between leak runs and controls, due in part to the large standard deviation of resistance change values. In contrast, in the present study, both the $R_{max}$ and $(R/T)_{max}$ of leak runs were statistically significantly different from controls (Table 2) indicating an improvement in sensitivity and specificity over the previous iteration of this modality. By housing the electrodes in a permeable porous matrix, we were able to decrease electrode-to-patient artifact without diminishing the ability of the electrodes to identify leaked saline and as a result greatly diminished the standard deviation of resistance changes in the presence of leak. We feel that this addition to EGLD will ultimately greatly enhance its usability in surgical patients.

For the electrolyte-gated leak detection (EGLD) system, the sensitivity of leak detection is improved by being able to set a high initial resistance baseline within the matrix surrounding the electrodes, as demonstrated in our most recent manuscript. In the experiments that follow, the matrix surrounding the resistance-measuring electrodes consisted of saline-impregnated polyurethane foam. Leaked electrolyte from, for example, a leak site in the gastrointestinal tract, that contacts the matrix surrounding the electrodes will be drawn into the matrix due to hydrostatic forces. The entry of that electrolyte into the porous matrix results in a drop in resistance in the matrix as detected by the embedded electrodes. The resistance value of the matrix as more and more electrolyte solution enters the matrix will ultimately approach the low resistance of the electrolyte solution itself. For this reason, if the initial baseline resistance of the matrix is very close to the resistance of the electrolyte solution, only a very small drop in resistance will be observed in the presence of leaked electrolyte entering the matrix around the electrodes, resulting in a lower probability of identifying a leak. Therefore, a method of being able to adjust the initial baseline resistance within an EGLD system would improve the sensitivity of leak detection. Furthermore, because the matrix-embedded electrodes are placed deep within the body of the patient at the time of surgery, a remote means of modulating the baseline resistance value within the porous matrix must be possible. In other words, a care-giver has to have the ability to set the baseline resistance from outside the patient's body, at the patient's bedside for example or in the ICU. The electrodes in these experiments represent a standard 4-electrode array of bioimpedance electrodes.

Figure 6:
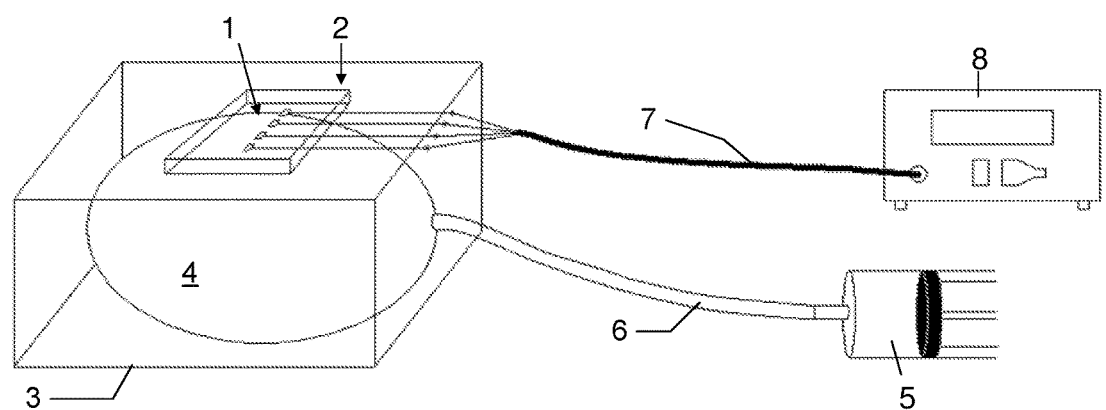
FIG. 6 shows an alternative apparatus for remote baseline resistance adjustment.

FIG. 6 shows an apparatus for remote baseline resistance adjustment. An array of four electrodes (1) within a saline-impregnated porous matrix (2) are contained within a housing (3) which in this experiment was a plastic box, however, the housing (3) could also be a surgical drain in which the electrodes and foam were housed in such a way as to have exposure to possible electrolyte leakage from a gastrointestinal leak site. Within the housing (3) is a balloon (4) which can be inflated or deflated remotely by a syringe (5) connected to the balloon by tubing (6). The electrodes transmit resistance data at the leak site via connecting wires (7) to a resistance measuring device (8).

Figure 7:
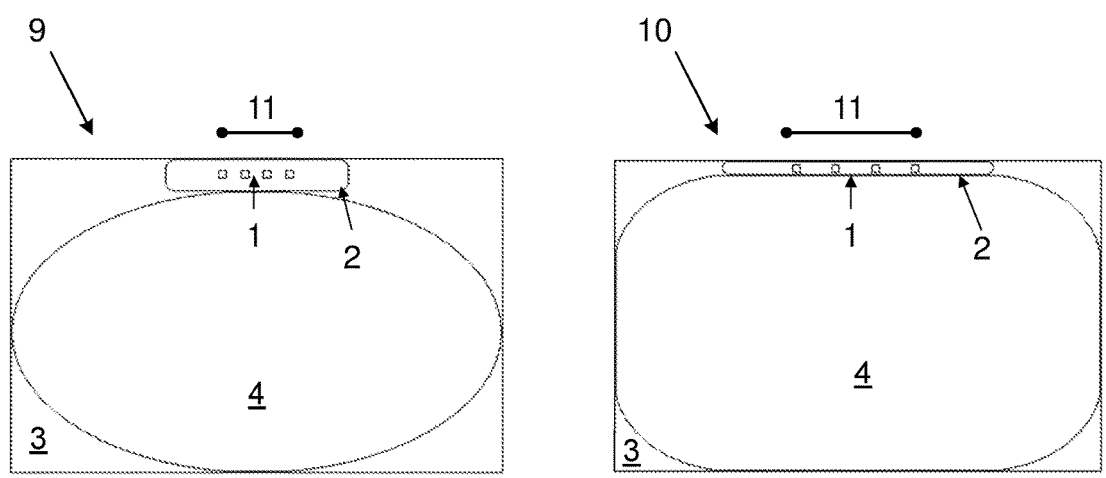
FIG. 7 shows a cross section of the apparatus from FIG. 6.

FIG. 7 shows a cross section of the apparatus from FIG. 6 in two configurations (9 and 10). In configuration (9), the electrodes (1) contained within the matrix (2) embedded in housing (3) contact balloon (4) with the balloon relatively deflated. In configuration (10), the balloon has been inflated via the remote syringe (FIG. 6, 10) which results in a flattening of the porous matrix (2). This results in extrusion of saline (not shown) from the porous matrix (2) as well as an increase in the distance between the electrodes (11).

Figure 8:
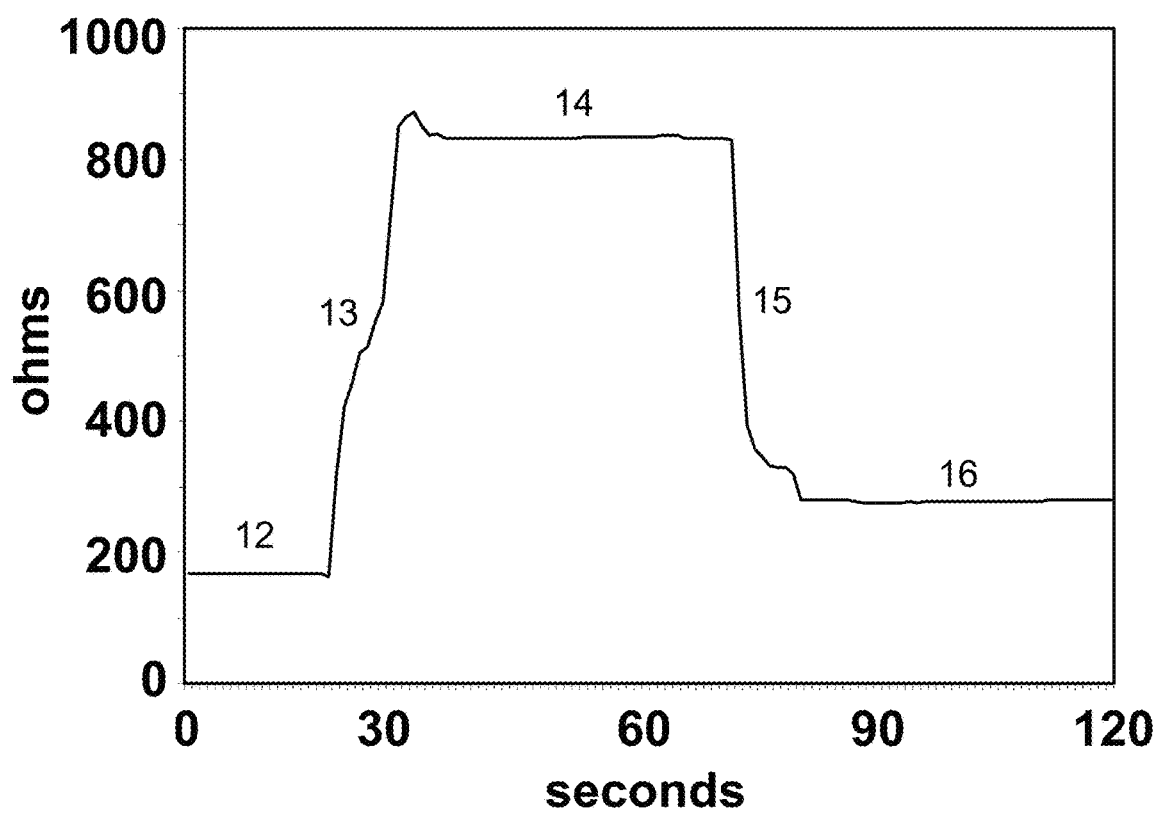
FIG. 8 shows experimentally obtained data in which a resistance baseline is established remotely.

FIG. 8 shows experimentally obtained data in which a resistance baseline is established remotely using the apparatus of FIGS. 6 and 7. The initial baseline value (12) corresponds to a porous matrix (FIGS. 6 and 7, 2) which is relatively saturated with electrolyte. An upstroke in resistance (13) corresponds to inflation of the balloon (FIGS. 6 and 7, 4) which leads to a compression of the porous matrix and extrusion of saline from the matrix as well as an increase in the distance between the electrodes (FIG. 7, 11). In FIG. 8, the extrusion of saline results in the establishment of a new resistance baseline (14) which is significantly higher than the initial baseline (12) due to the extrusion of saline from the matrix. Leaked electrolyte, representing a gastrointestinal leak test in the presence of a leak, is then absorbed by the porous matrix leading to a downstroke in resistance (15) from the new baseline finally coming to rest at the final baseline (16), confirming the presence of leak.

Figure 9:
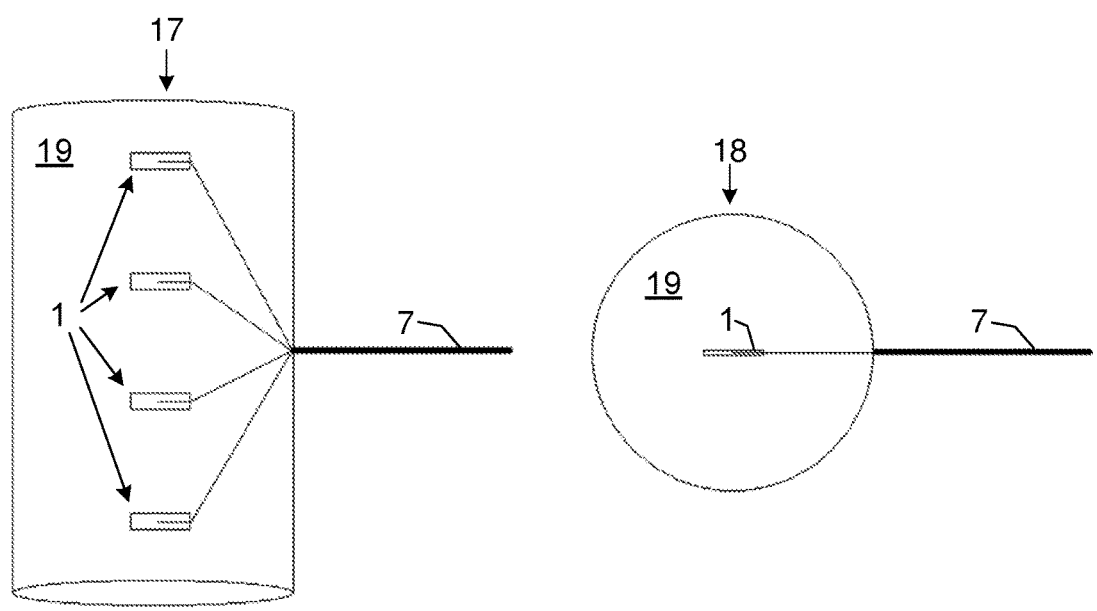
FIG. 9 shows an alternate apparatus for remote baseline establishment in top view and side view.
Figure 10:
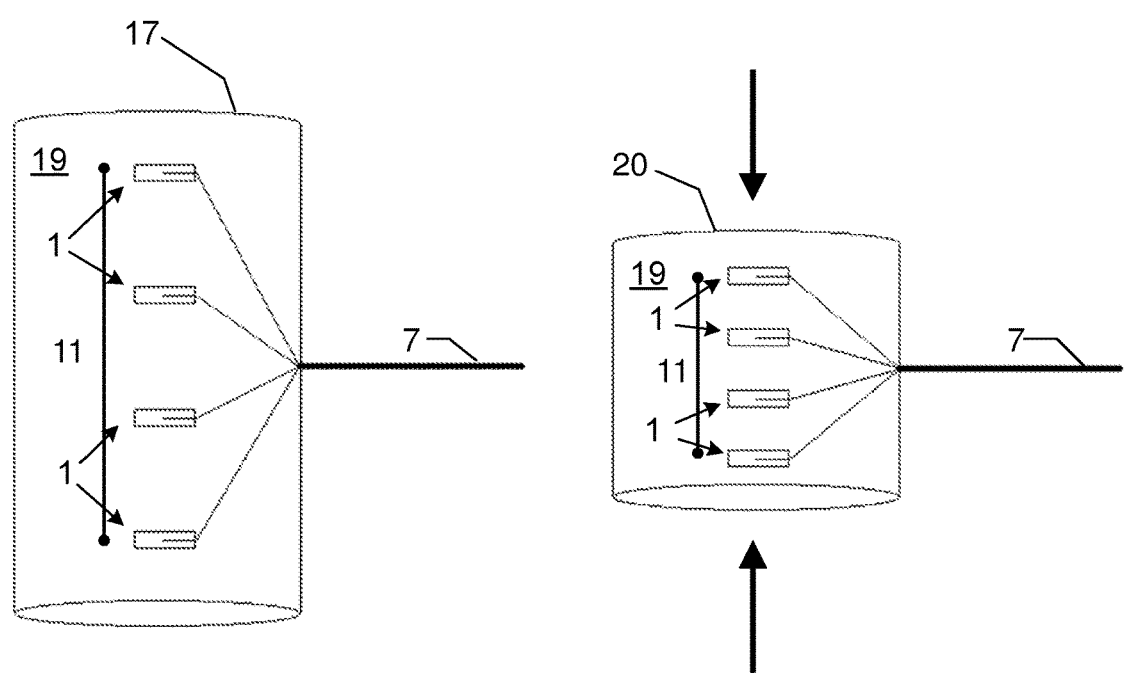
FIG. 10 shows the same apparatus as in FIG. 9 in neutral conformation and compressed conformation.

FIG. 9 shows an alternate apparatus for remote baseline establishment in top view (17) and side view (18). In this case, the electrode array (1) is housed in a cylindrical porous matrix (19). The electrodes are attached by connecting wires (7) to an impedance measuring unit (not shown). FIG. 10 shows the same apparatus as in FIG. 9 in neutral conformation (17) and compressed conformation (20), with the arrows in (20) indicating axial compression of the cylindrical porous matrix (19). This results in compression of the foam with extrusion of saline (not shown) and a decrease in the distance between the electrodes (11).

Figure 11:
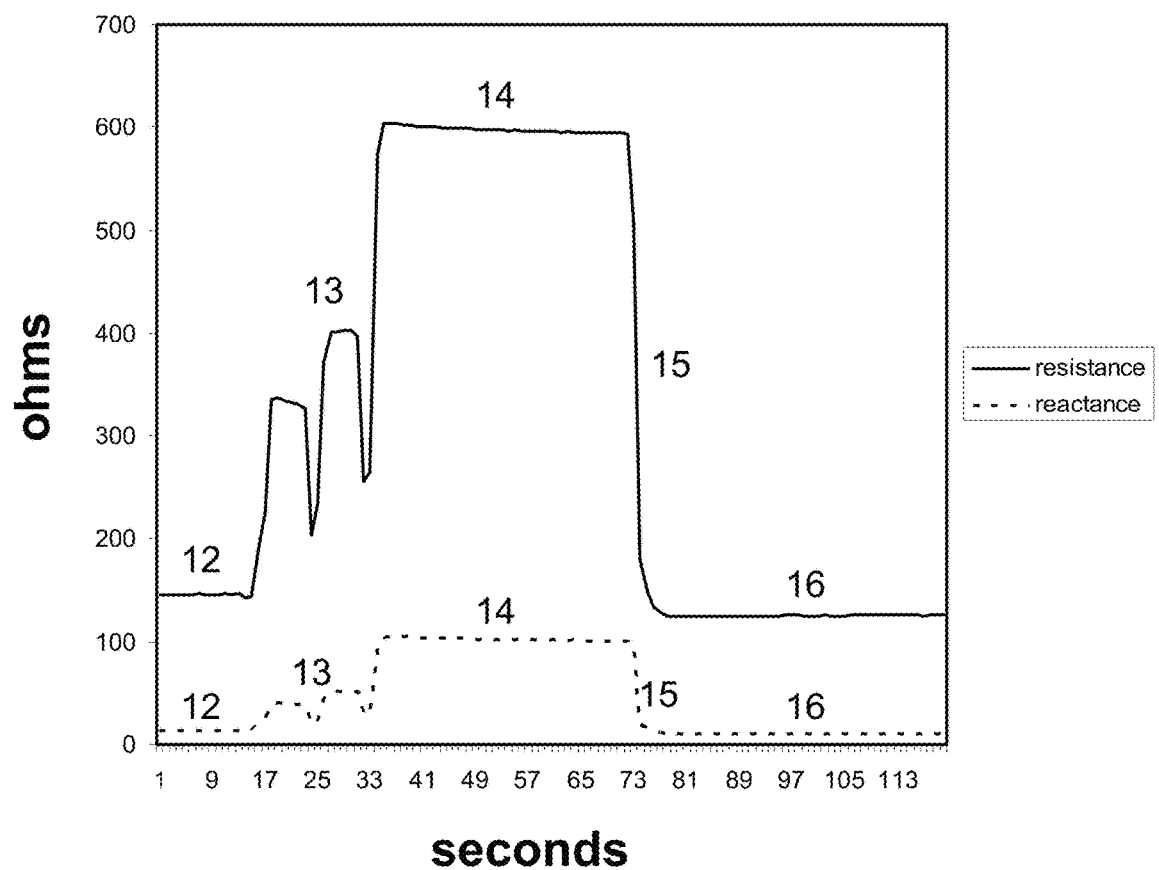
FIG. 11 shows experimentally obtained data in which a resistance baseline is established remotely using the apparatus of FIGS. 9 and 10.

FIG. 11 shows experimentally obtained data in which a resistance baseline is established remotely using the apparatus of FIGS. 9 and 10. The initial baseline value (12) corresponds to a porous matrix (FIGS. 9 and 10, 19) which is relatively saturated with electrolyte. An upstroke in resistance (13) corresponds to axial compression of the matrix (FIG. 10, 20)) which leads to a compression of the porous matrix and extrusion of saline from the matrix as well as a decrease in the distance between the electrodes (FIG. 10, 11). In FIG. 11, the extrusion of saline results in the establishment of a new resistance (14) which is significantly higher than the initial baseline (13) due to the extrusion of saline from the matrix. Leaked electrolyte, representing gastrointestinal leak, is then absorbed by the porous matrix leading to a downstroke in resistance (15) from the new baseline finally coming to rest at the final baseline (16), confirming the presence of leak. Resistance (FIG. 11, solid curve) and capacitive reactance (FIG. 11, dashed curve) both demonstrate similar patterns of change in response to matrix compression.

Figure 12:
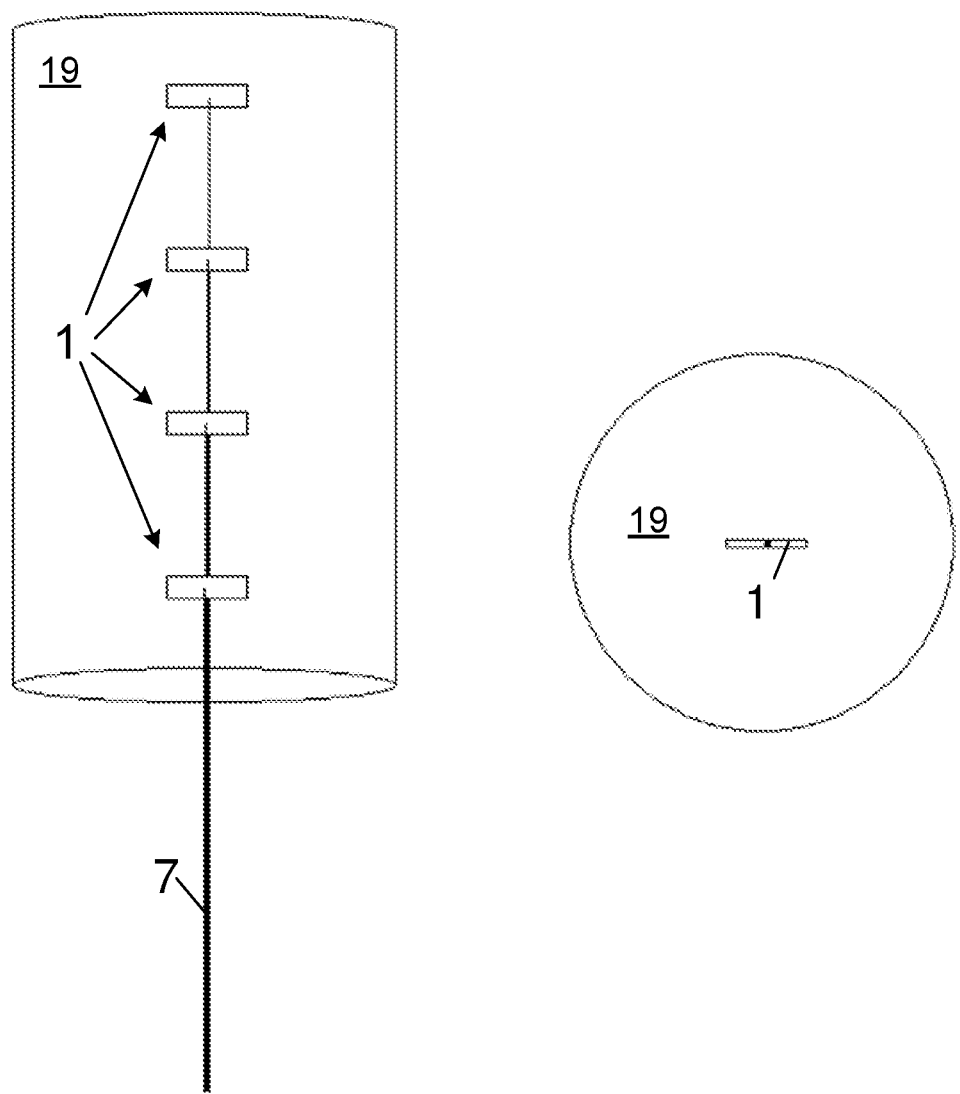
FIGS. 12-14 depict alternate configurations of the porous matrix housing.

FIG. 12 demonstrates that the connecting wires (7) that connect the electrodes (1) to the impedance measuring device (not shown) can be configured to exit the cylindrical porous matrix (19) through the base of the cylinder instead of the side.

Figure 13:
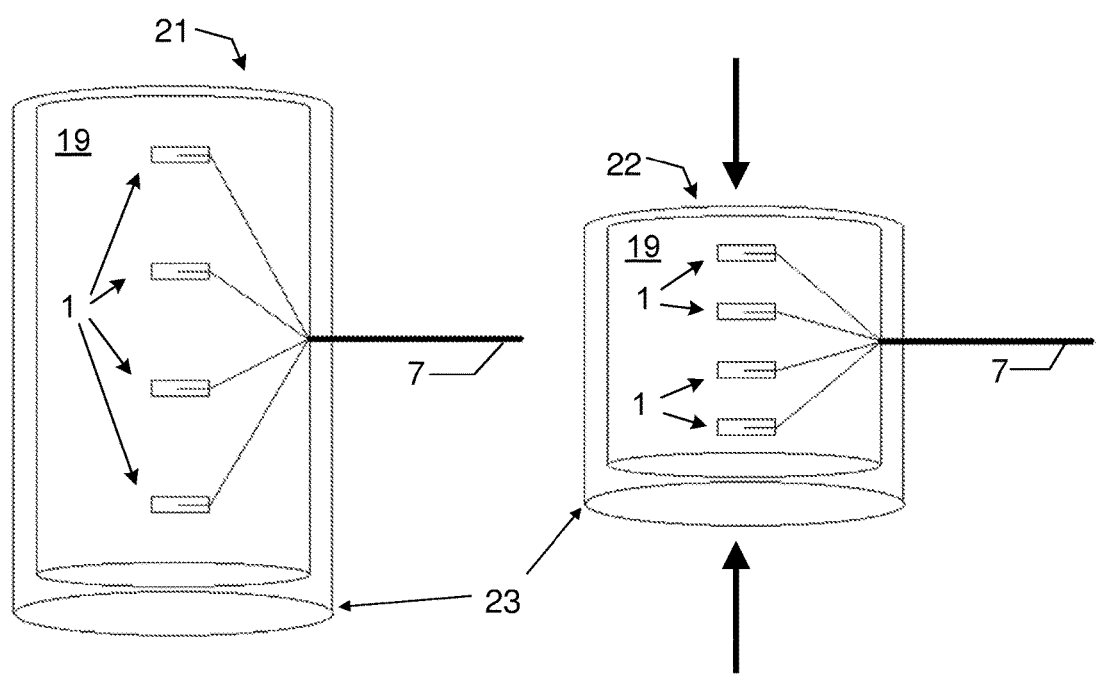

FIG. 13 demonstrates the electrodes (1) and connecting wires (7) embedded in a cylindrical saline-soaked porous matrix (19) in two configurations: neutral (21) and contracted (22). In this configuration, the entire porous matrix is covered in a material (23) that prevents irreversible extrusion of electrolyte from the matrix and effectively seals the matrix so that electrolyte cannot escape. Instead, electrolyte is only temporarily extruded from the matrix during compression then re-absorbed when compression ceases. In this apparatus, resistance and reactance changes are not due to direct contact with the environment but are due to mechanical action of the environment on the isolated electrical milieu of the sealed porous matrix to alternately extrude and reabsorb electrolyte from the matrix.

Figure 14:
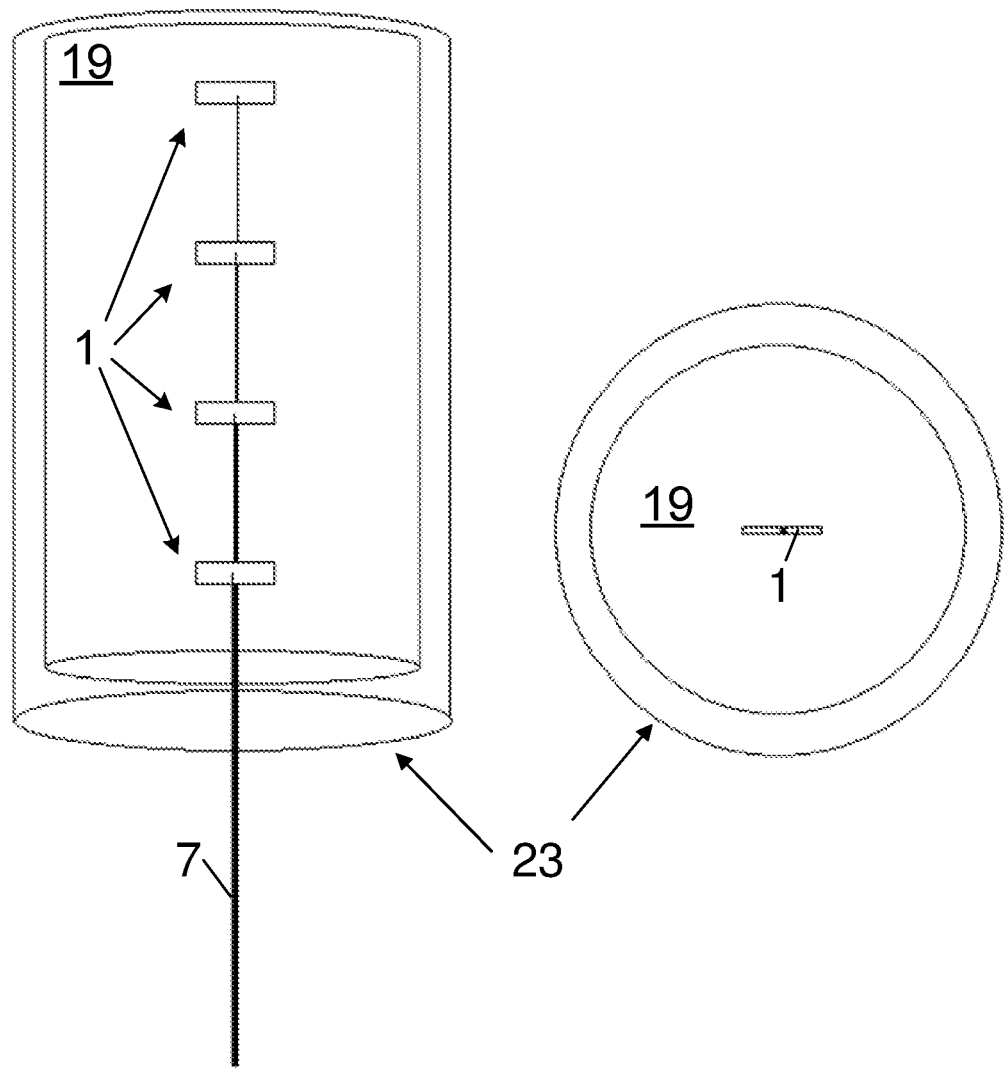

FIG. 14 demonstrates that the connecting wires (7) that connect the electrodes (1) to the impedance measuring device (not shown) can be configured to exit the cylindrical porous matrix (19) through the base of the cylinder instead of the side, covered by a material that seals the matrix (23) to prevent irreversible extrusion of electrolyte from the matrix.

Figure 15:
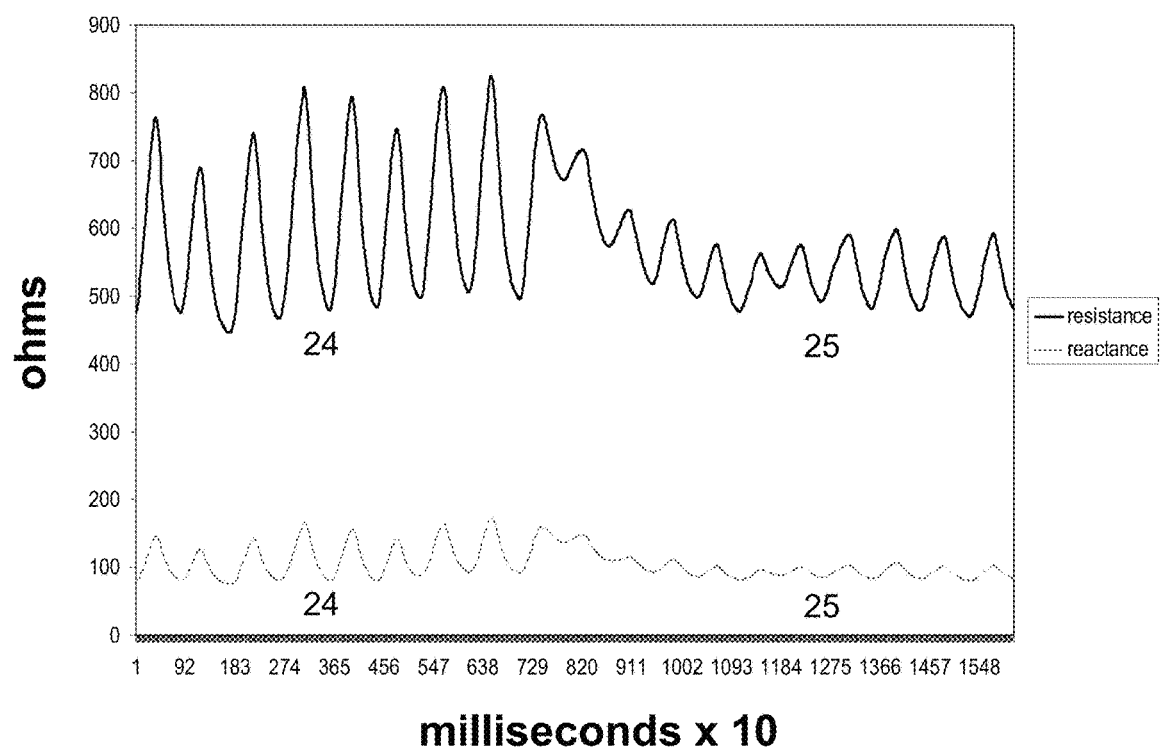
FIG. 15 shows experimentally derived data using the apparatus described in FIG. 13 to approximate, in an ex vivo model, the measurement of cardiac contractility.

FIG. 15 shows experimentally derived data using the apparatus described in FIG. 13 to approximate, in an ex vivo model, the measurement of cardiac contractility. Measuring cardiac contractility is important because a decrease in this value ultimately represents pump failure of the heart. Cardiac contractility presently is only measurable indirectly via the assessment of blood pressure in the systemic or pulmonary vasculature, or by cardiac output measurement, all of which represent downstream effects of contractility. Direct measurement of cardiac contractility could represent a means of earlier identification of cardiac failure allowing for earlier intervention. Decreases in cardiac contractility may occur due to myocardial ischemia, rejection or reperfusion injury in the case of cardiac transplantation, fluid overload in the case of congestive heart failure, or other injury or pathology of the myocardium. In FIG. 15, two curves are represented, the dark line representing resistance and the lighter curve representing reactance changes in the sealed porous matrix cylinder from FIG. 13 as sensed by the electrodes. In this ex vivo model, a regular heartbeat of 60 beats per minute is approximated by a 5 ml amplitude displacement of the bases of the cylindrical porous matrix in a contraction/relaxation cycle with a frequency of 1 Hz (24). A transition to a state of decreased contractility is represented by (25) at which time the amplitude of the contraction/relaxation cycle decreases to 2.5 ml, resulting in a decreased amplitude of the cycling of the resistance and reactance curves (FIG. 15, dark and light curves). FIG. 15 represents a situation in which normal contractility (24) transitions to pathologically decreased contractility (25) and demonstrates the ability of the apparatus in FIG. 13 to detect this change. Both resistance change (dark curve) and reactance change (lighter curve) demonstrate similar amplitude changes in response to the decreased contractility. In vivo, the apparatus of FIG. 13 would be able to register changes in cardiac contractility if it were embedded in or otherwise affixed to the interior or exterior of the myocardium (see FIGS. 19-22). This could be accomplished internally through cardiac catheterization, in the same way pacemaker wires are embedded in the myocardium, or externally at the time of heart surgery or transplantation by embedding the apparatus in the myocardium or on the surface of the epicardium, as pacing wires are attached to the heart at the time of heart surgery. Wires could be attached to a pacing device or brought out through the skin to attach to the impedance measuring device.

Figure 16:
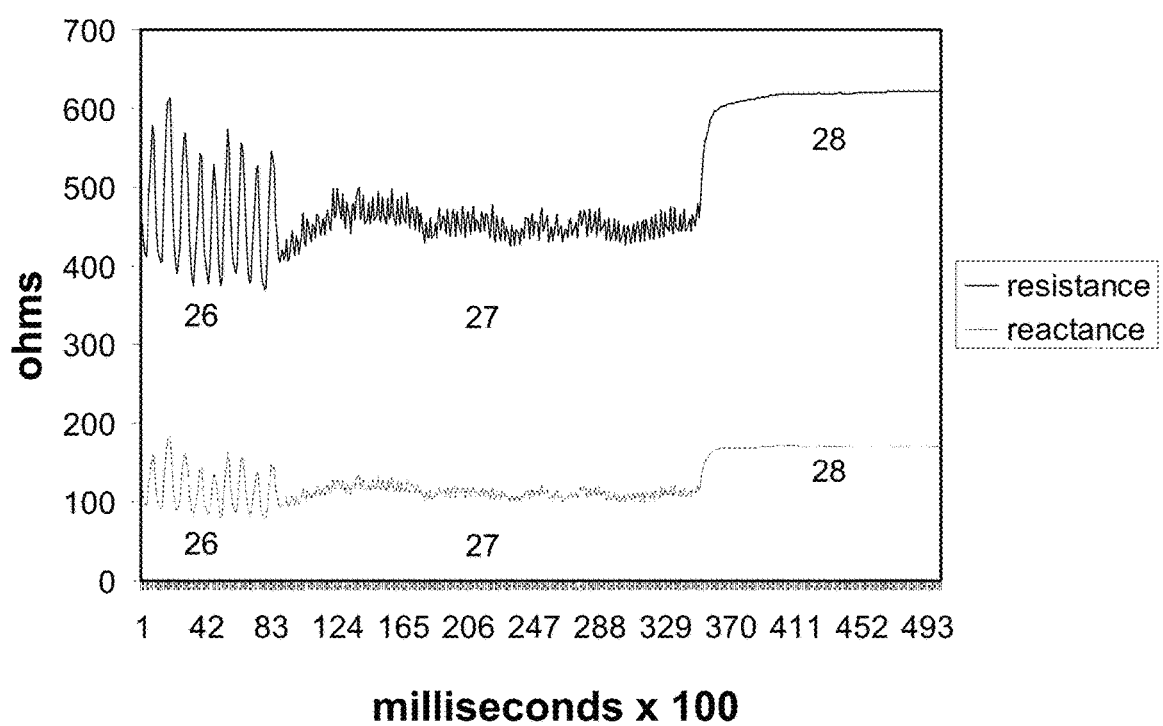
FIG. 16 depicts additional experimental data derived from the apparatus of FIG. 13 demonstrating the resistance and reactance changes associated with a model of ventricular tachycardia progressing to asystole.

FIG. 16 is additional experimental data derived from the apparatus of FIG. 13 demonstrating the resistance and reactance changes associated with a model of ventricular tachycardia progressing to asystole using the same ex vivo method of foam cylinder matrix compression as used in FIG. 15. At (26), a regular heartbeat of 60 beats per minute is generated by the ex vivo compression system as above followed by transition to a heartbeat of 180 beats per minute with the same amplitude (displacement of the bases of the cylinder of 5 ml) at (27) representing ventricular tachycardia and finally asystole, or 0 beats per minute, at (28), resulting in readily identifiable changes in resistance (dark curve) and reactance (lighter curve).

Figure 17:
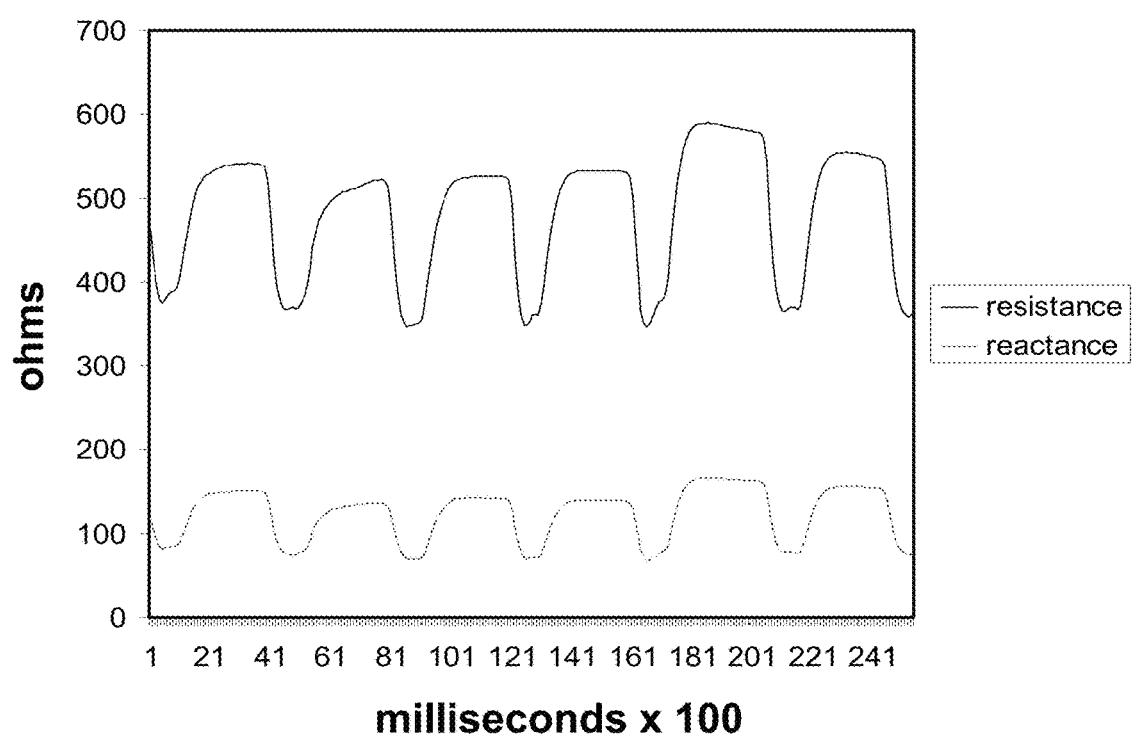
FIGS. 17 and 18 depict experimentally derived data using the apparatus described in FIG. 13 to approximate, in an ex vivo model, lung compliance.
Figure 18:
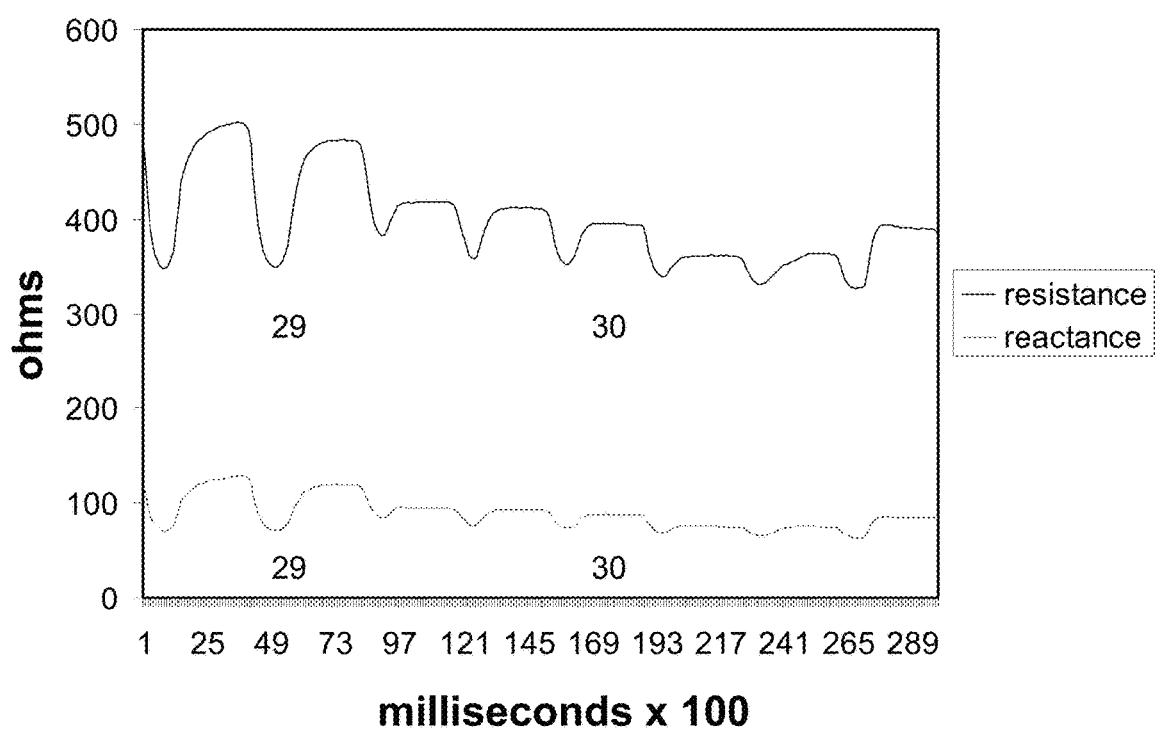

FIG. 17 and FIG. 18 demonstrate experimentally derived data using the same apparatus in FIG. 13 using the same ex vivo model of foam cylinder matrix compression in FIGS. 15 and 16. In these figures, lung compliance is modeled. Lung compliance, like cardiac contractility, may decrease in certain pathologic states such as pulmonary edema, pulmonary injury, pulmonary infection, respiratory distress syndrome, or graft rejection or ischemia/reperfusion injury after lung transplant. In vivo, the apparatus of FIG. 13 would be able to register changes in lung compliance if it were embedded in or otherwise affixed to the interior or exterior of the lung tissue (see FIGS. 23-25). This could be accomplished internally through bronchoscopy or externally at the time of chest tube placement, lung surgery or transplantation by embedding the apparatus in the lung parenchyma or on the surface of the lung or in the pulmonary fissures, as chest tubes are placed at surgery or at the bedside or in the ICU. Wires could be attached to an internal impedance measuring device in the body in a similar location to a pacemaker, or brought out through the skin to attach to the impedance measuring device. In FIG. 17 a respiratory cycle representing normal lung compliance is modeled. In FIG. 18, normal lung compliance (29) progresses to decreased lung compliance (30) through a decrease in the volumetric compression of the foam cylinder matrix as detected by the impedance electrodes (FIG. 13). In both FIGS. 17 and 18 resistance (dark curves) and reactance (lighter curves) demonstrate similar patterns of change.

Figure 23:
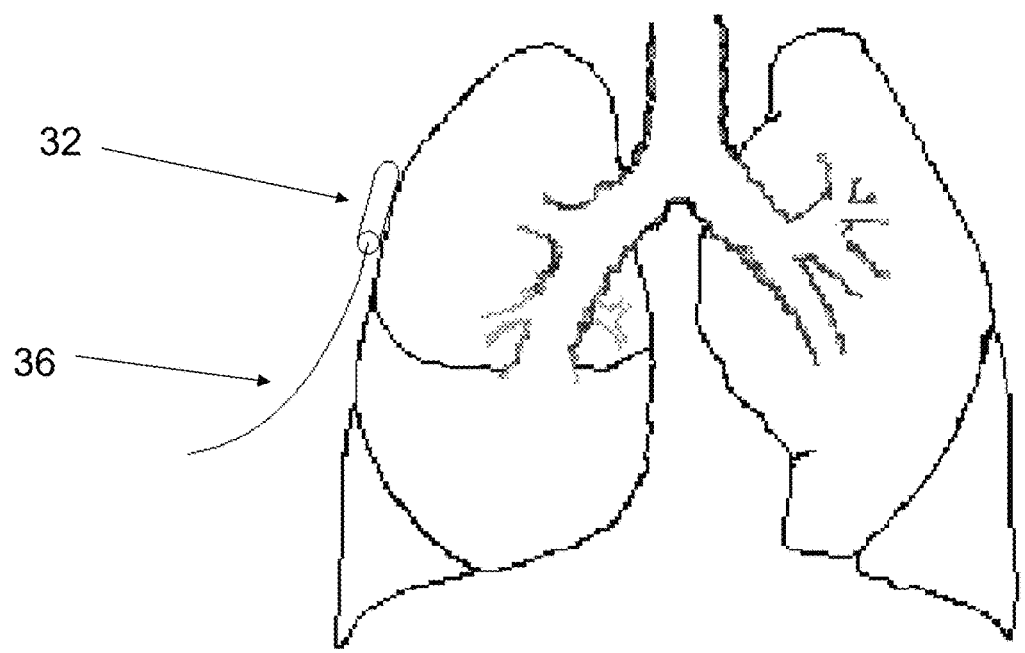
FIGS. 23-25 are theoretical depictions of a heart in which a sealed cylindrical matrix containing electrodes are disposed in various portions of the heart.

In FIGS. 15-18, the key difference in the apparatus is the addition of a barrier to electrolyte extrusion (FIGS. 13 and 14, 23). This prevents the drift of measurements that would result if electrolyte were irreversibly extruded from the porous matrix when compressed and allows the impedance changes to be based principally on the changes of electrolyte density in the matrix as produced by compression and relaxation of the matrix.

The apparatus of FIG. 13 could also be deployed in other tissues to measure pathologic changes in those tissues as a result of edema, ischemia, infection, rejection, or other pathology. Other potential target tissues could be: limb tissues after injury or vascular surgery; liver after resection, repair, or transplantation; kidney after resection, repair or transplantation; brain after trauma or surgery; eye after trauma or surgery; major blood vessels including the aorta, etc. after trauma or surgery; other abdominal viscera including intestine after trauma or surgery; or an appropriately sized probe could be delivered intravascularly to measure intravascular pressure.

Figure 19:
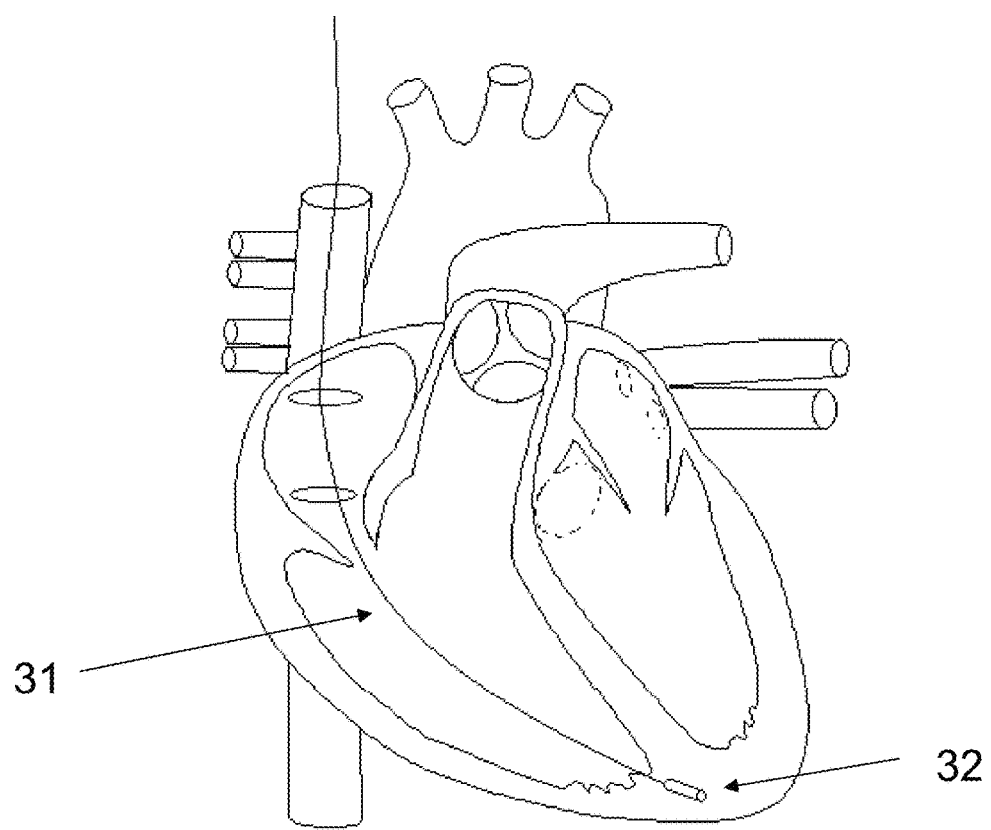
FIGS. 19-22 are theoretical depictions of a heart in which a sealed cylindrical matrix containing electrodes are disposed in various portions of the heart.

FIG. 19 shows a depiction of a heart in which a right heart catheter (31) delivers a sealed cylindrical matrix containing electrodes (32) as illustrated in detail in FIG. 14 into the myocardium for contractility/rhythm measurements. The catheter (31) contains connecting wires that attach to an impedance measuring device (not shown).

Figure 20:
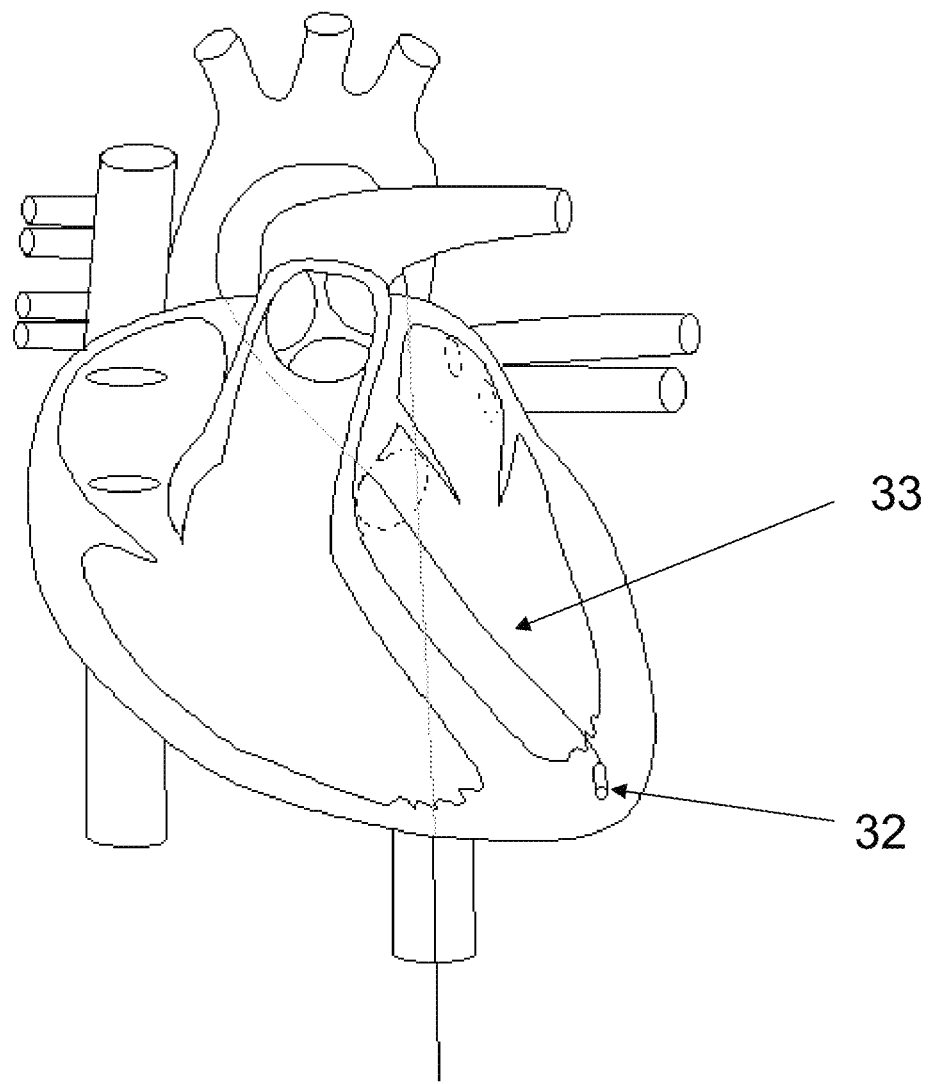

FIG. 20 shows a depiction of a heart in which a left heart catheter (33) delivers a sealed cylindrical matrix containing electrodes (32) as illustrated in detail in FIG. 14 into the myocardium for contractility/rhythm measurements. The catheter (33) contains connecting wires that attach to an impedance measuring device (not shown).

Figure 21:
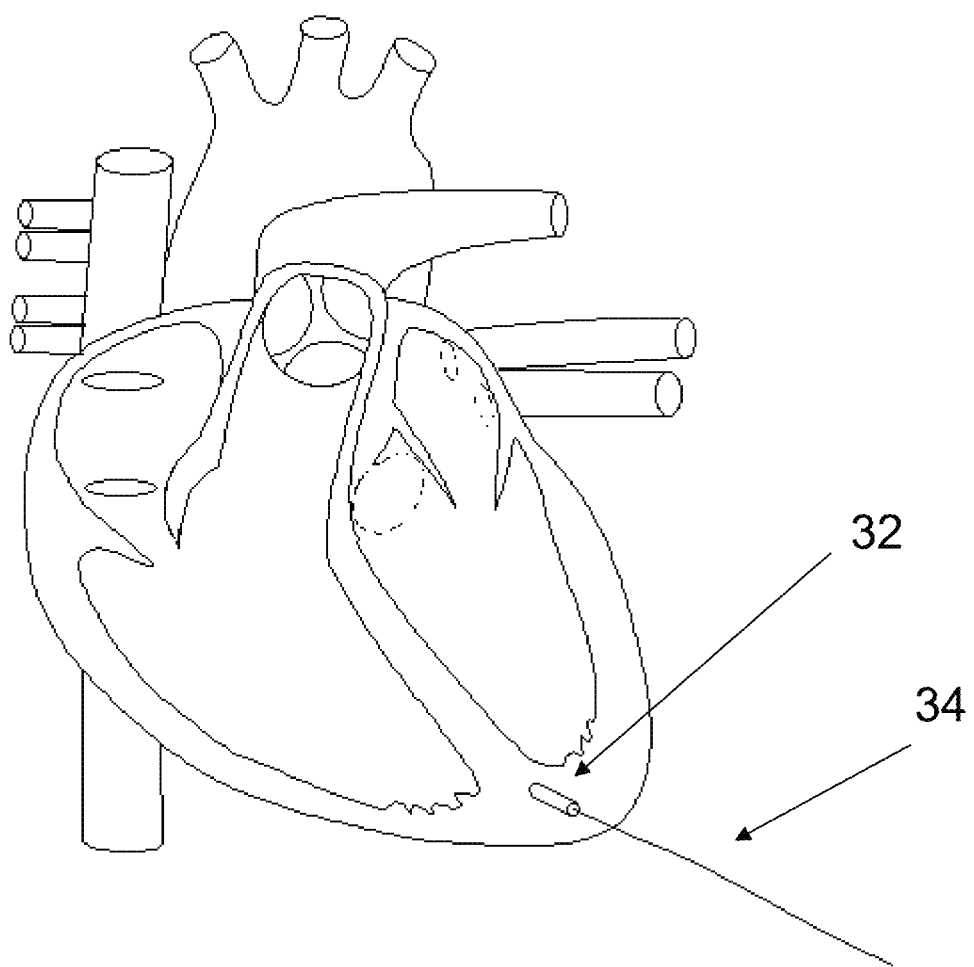

FIG. 21 shows a depiction of a heart in which a surgically placed heart catheter (34) delivers a sealed cylindrical matrix containing electrodes (32) as illustrated in detail in FIG. 14 into the myocardium for contractility/rhythm measurements. The catheter (34) contains connecting wires that attach to an impedance measuring device (not shown).

Figure 22:
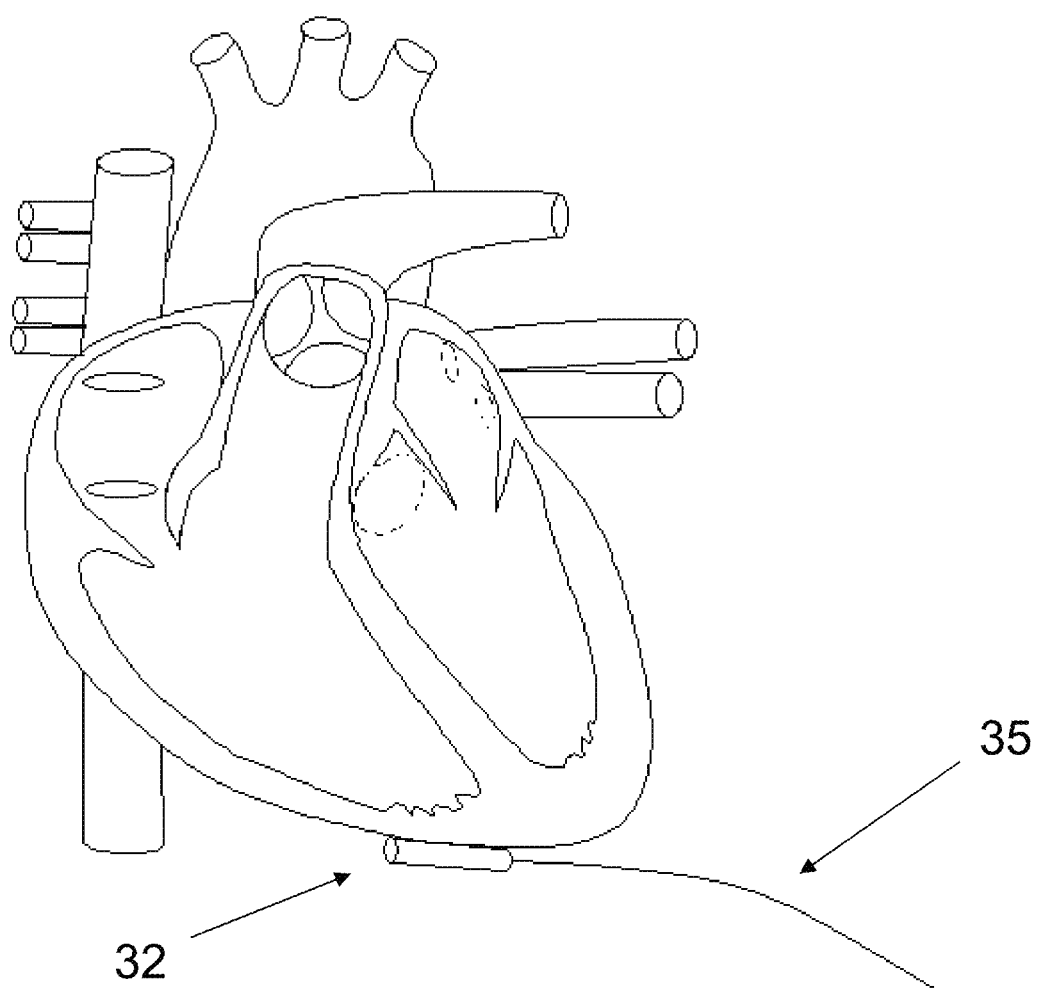

FIG. 22 shows a depiction of a heart in which a surgically placed heart catheter (35) delivers a sealed cylindrical matrix containing electrodes (32) as illustrated in detail in FIG. 14 onto the surface of the epicardium for contractility/rhythm measurements. The catheter (35) contains connecting wires that attach to an impedance measuring device (not shown).

FIG. 23 shows a depiction of the lungs in which a surgically or percutaneously placed catheter (36) delivers a sealed cylindrical matrix containing electrodes (32) as illustrated in detail in FIG. 14 onto the visceral pleural surface for lung compliance measurements. The catheter (36) contains connecting wires that attach to an impedance measuring device (not shown).

Figure 24:
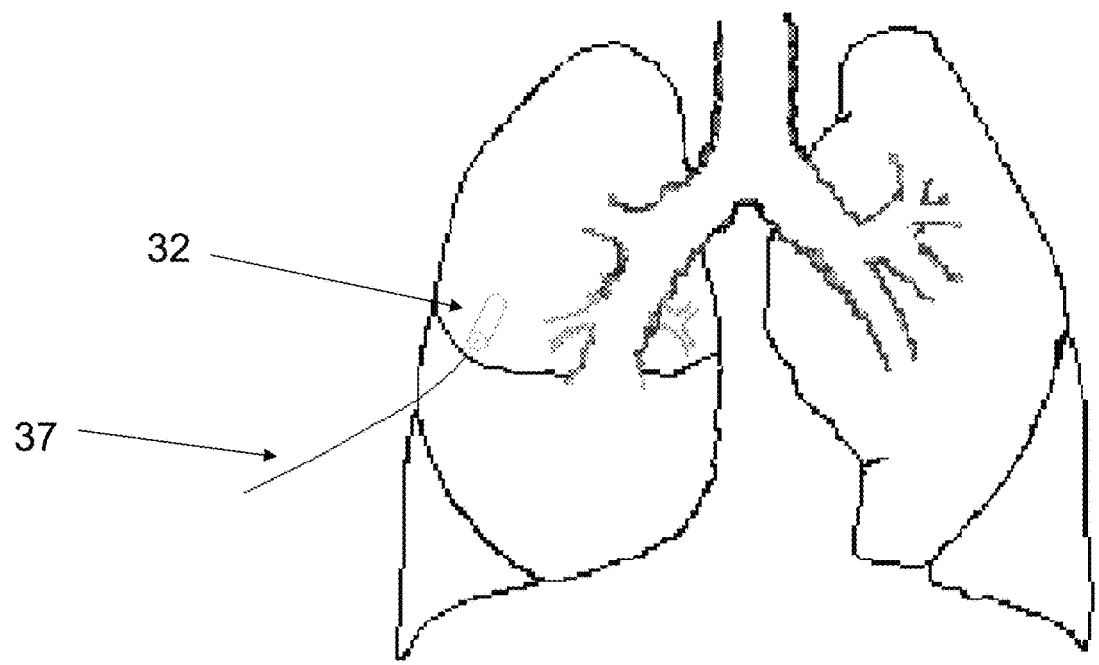

FIG. 24 shows a depiction of the lungs in which a surgically or percutaneously placed catheter (37) delivers a sealed cylindrical matrix containing electrodes (32) as illustrated in detail in FIG. 14 into a fissure of the lung between two lobes for lung compliance measurements. The catheter (37) contains connecting wires that attach to an impedance measuring device (not shown).

Figure 25:
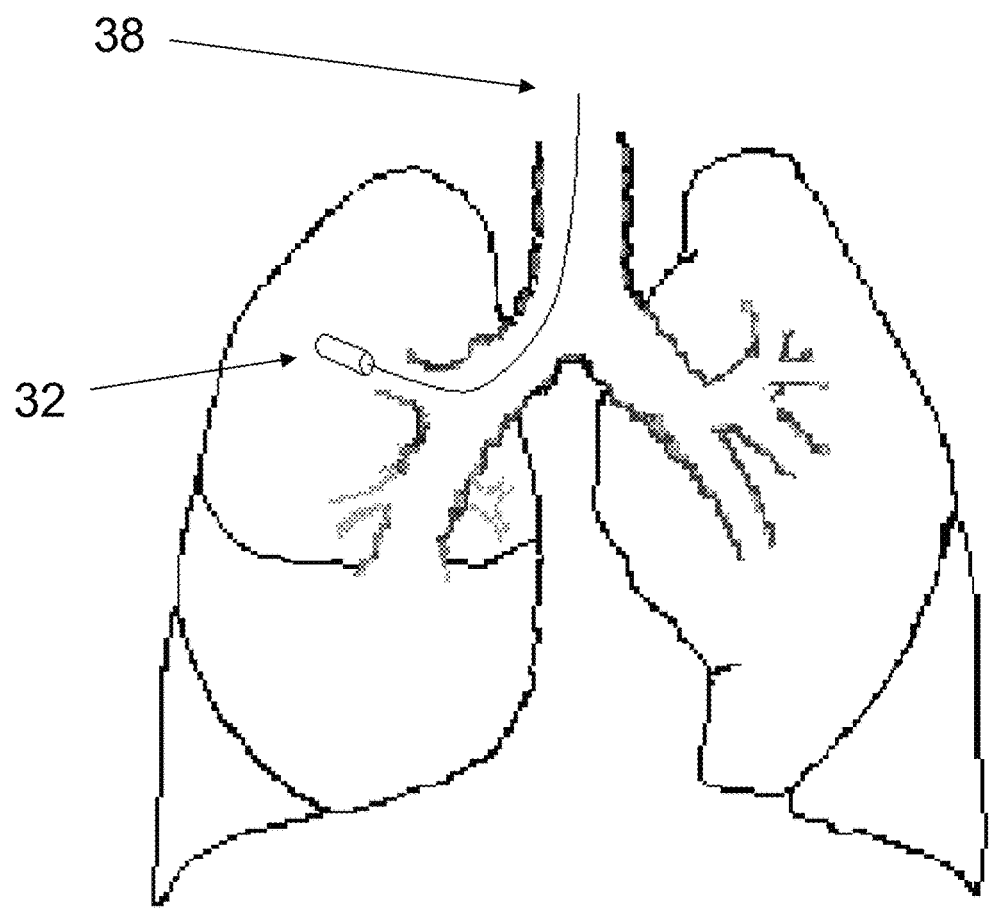

FIG. 25 shows a depiction of the lungs in which a bronchoscopically placed catheter (38) delivers a sealed cylindrical matrix containing electrodes (32) as illustrated in detail in FIG. 9 into the lung parenchyma for lung compliance measurements. The catheter (38) contains connecting wires that attach to an impedance measuring device (not shown).

Figure 26:
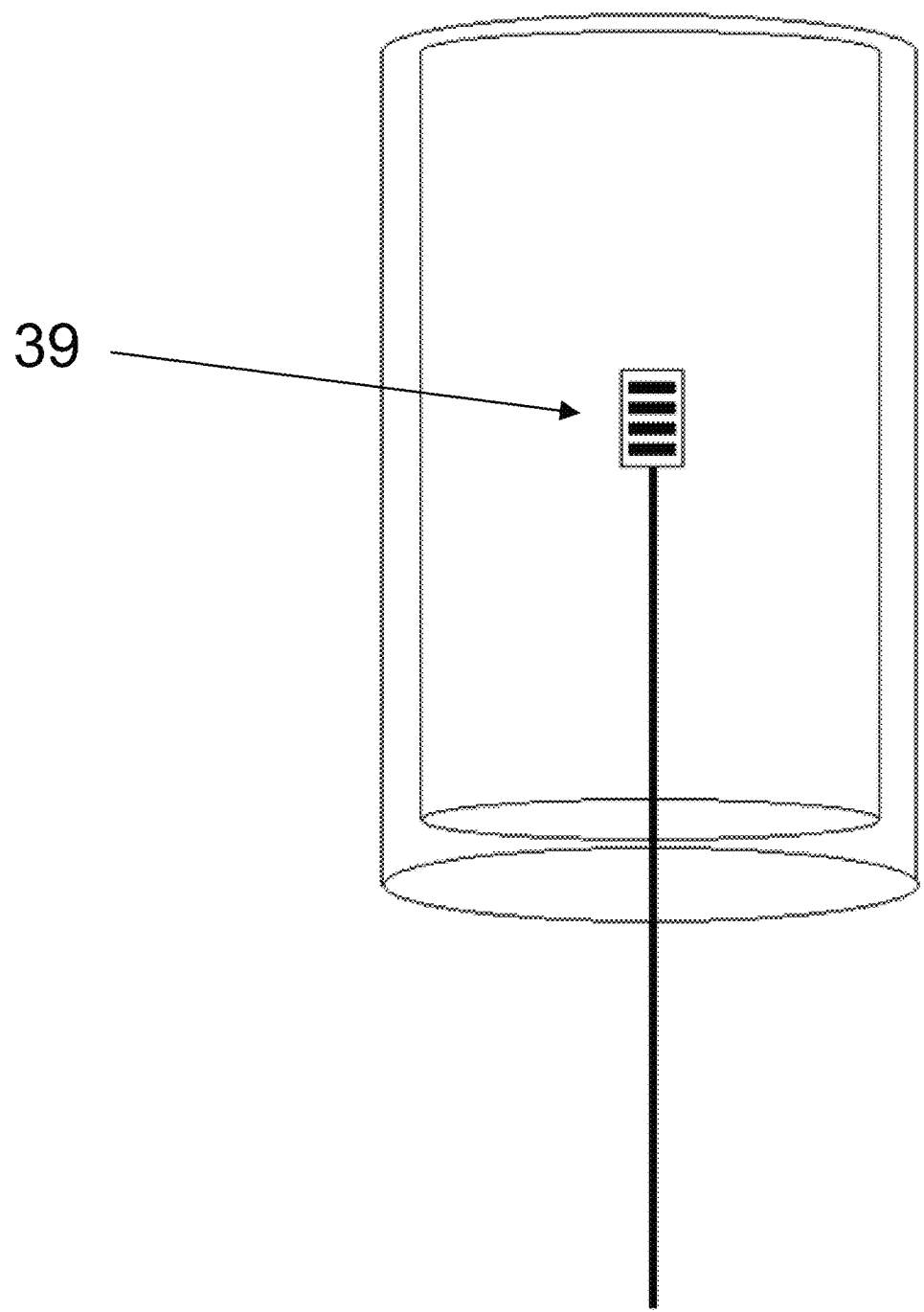
FIG. 26 depicts an alternate embodiment of the porous matrix housing.

FIG. 26 shows another embodiment of the apparatus of FIG. 14 in which the electrodes are affixed to an inflexible scaffold (39) embedded within the porous matrix. In this embodiment, compression of the porous matrix only results in a change in electrolyte density in the porous matrix and not a change in the distance between the electrodes.

In other embodiments, the porous matrix can be replaced by a flexible, electrically conducting silicone, or hydrogel, strain-dependent carbon nanotubes, or conductors, semiconductors or other materials that are flexible and allow for an enclosed electrical milieu for electrodes and that change in their resistance and reactance in response to mechanical changes imposed on them by their surroundings.

Figure 27:
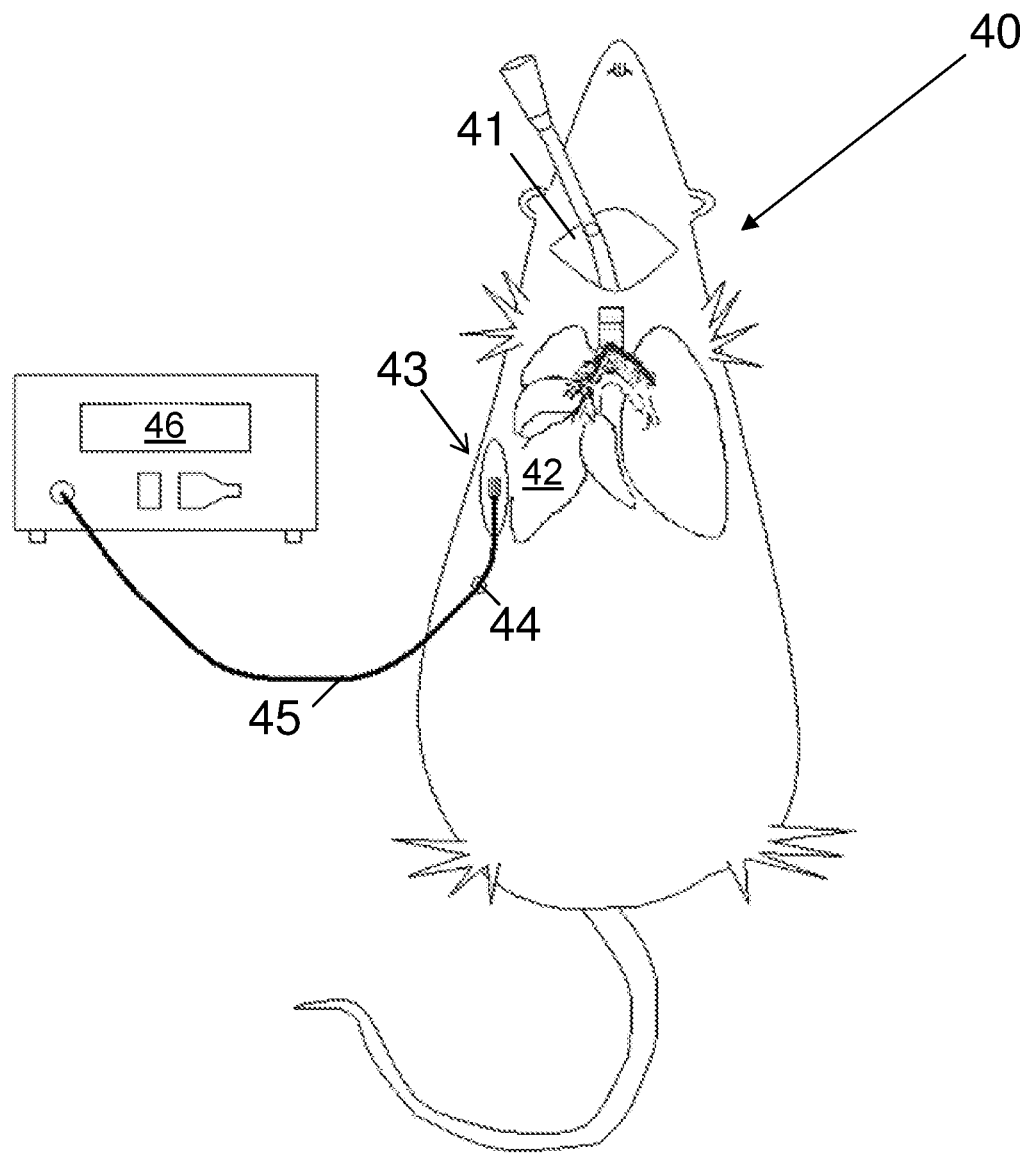
FIG. 27 illustrates the apparatus attached to an animal.

FIG. 27 illustrates an actual experimental animal demonstrating the functionality of a version of the apparatus described in FIG. 26 following the deployment method described in FIG. 23 in which a percutaneously placed catheter delivers a sealed matrix containing electrodes onto the visceral pleural surface for lung compliance measurements. In this experiment, an anesthetized rat (40) was placed on a small animal ventilator (not shown) via a tracheostomy using a 16 gauge angiocathter placed into the trachea (41). A median sternotomy was performed to expose the right lung (42). The lung compliance sensor containing the matrix-embedded electrodes (43) was then placed in direct contact with the visceral pleural surface of the right lung (42). For this experiment, the matrix consisted of sodium polyacrylate hydrogel with Parafilm used to seal the hydrogel-surrounded electrodes. Through a puncture incision in the lateral chest wall (44) the connecting wires (45) were brought extracorporeally and connected to an impedance monitoring device (46). Ventilatory support delivered via a small animal ventilator consisted of a set respiratory rate of 66 breaths per minute and a tidal volume of 3.6 ml.

Figure 28:
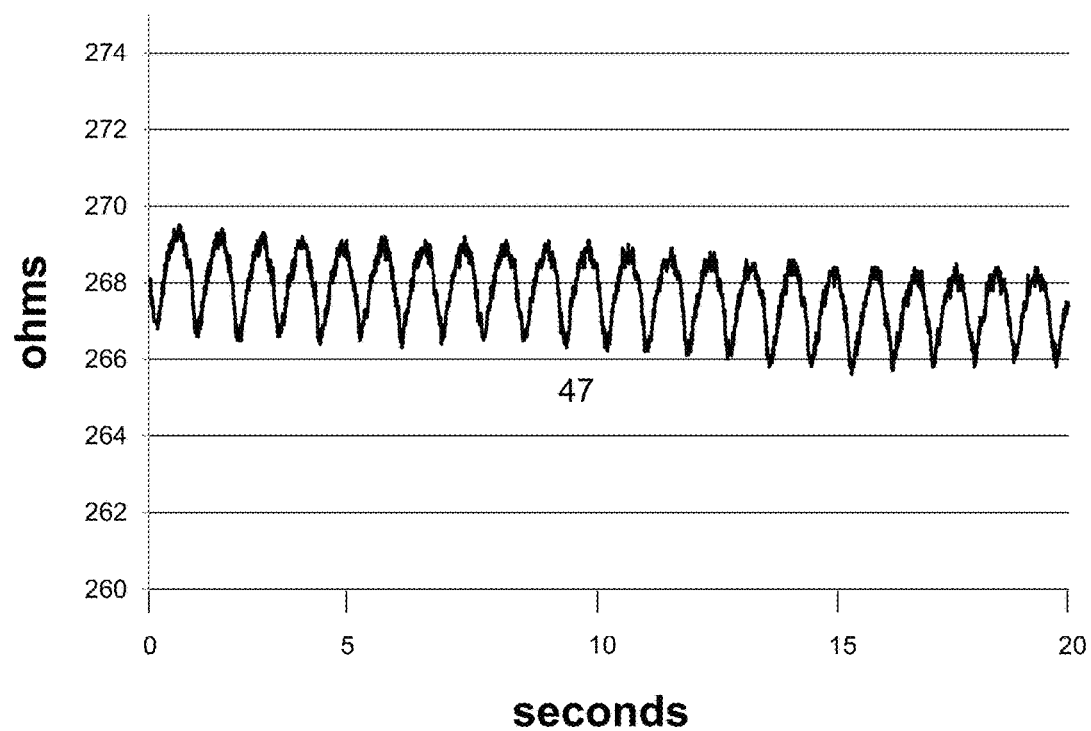
FIG. 28 depicts experimentally derived data from the experimental animal illustrated in FIG. 27.

FIG. 28 demonstrates experimentally derived data from the experimental animal illustrated in FIG. 27. Expansion of a normally compliant lung against the matrix-embedded electrodes results in a readily measureable regular cycle of resistance change (only resistance and not reactance is illustrated). In theory, this could be used to track the compliance, expansion, or ventilation of the lung over time with decreases in any of these clinical parameters resulting in a decrease in the amplitude of the measured electrical resistance cycle. The advantage to this apparatus is that precise lung compliance measurements are possible by simple contact with the lung tissue in a way that minimizes injury to the lung tissue. This apparatus could be mounted on a pleural catheter or chest tube for continuous compliance measurements in patients in the ICU or medical or surgical wards. It could be used to track lung expansion/ventilation and/or the development of pulmonary edema in patients who have recently undergone lung surgery or transplantation or chest trauma.

Figure 29:
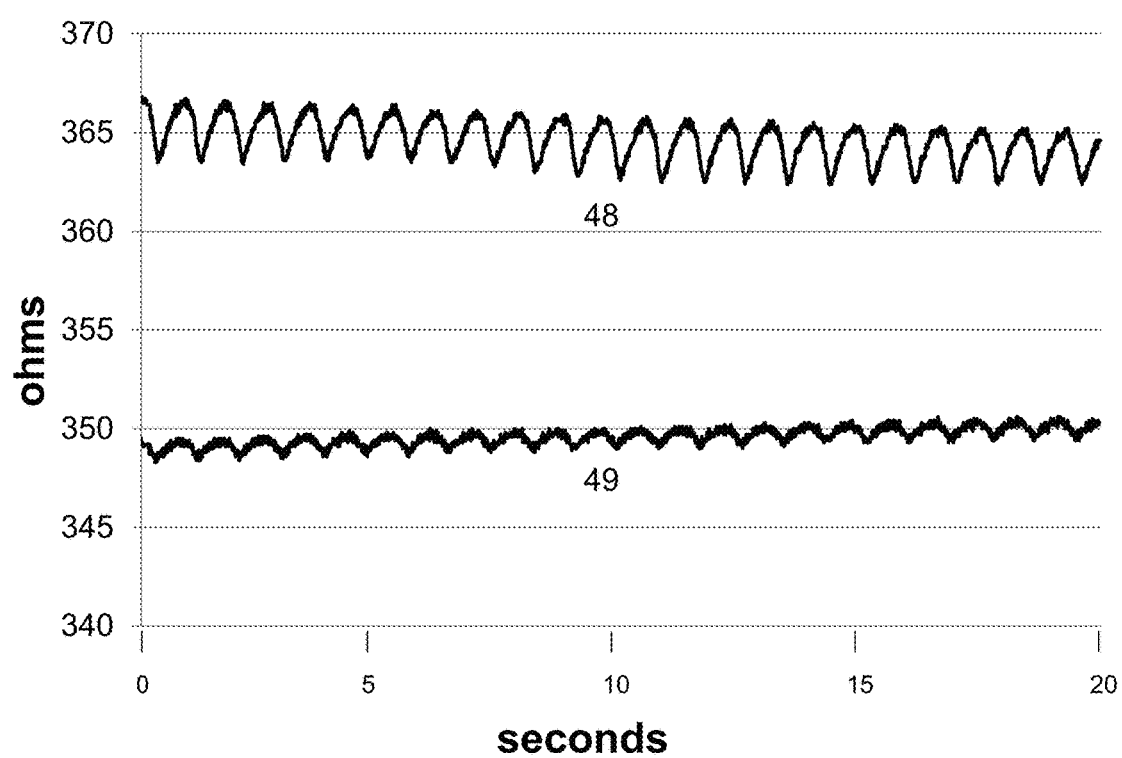
FIG. 29 depicts experimentally derived data from a small animal ventilator.

FIG. 29 demonstrates experimentally derived data from an additional experimental animal as illustrated in FIG. 27 under general anesthesia on a small animal ventilator at a tidal volume of 3.5 ml and respiratory rate of 65 breaths per minute. Expansion of a normally compliant lung against the matrix-embedded electrodes results in a readily measureable regular cycle of resistance change with an amplitude of approximately 3 ohms (48). The right mainstem bronchus of the same experimental animal was then clamped to prevent ventilation of the right lung and the tidal volume was decreased to 2.5 ml to mimic the pathologic condition of lung collapse either due to pneumothorax or endobronchial mucous plugging. Under these conditions, the amplitude of resistance change detected by the compliance measurement sensor was decreased to an amplitude of approximately 1 ohm (49). This demonstrates the ability of the compliance sensor to detect pathologic changes in the lung with a high degree of sensitivity.

Figure 30:
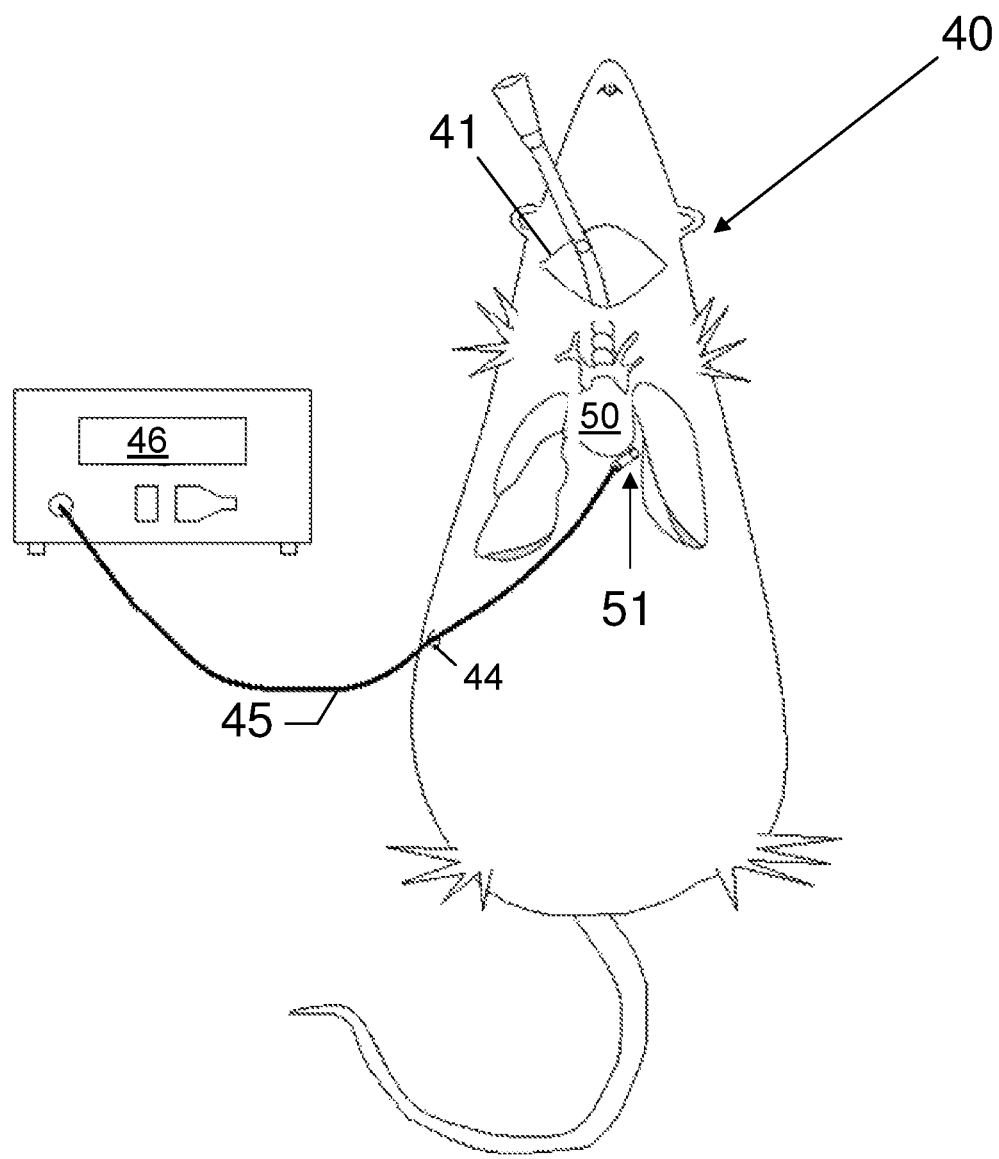
FIG. 30 depicts an alternate embodiment of an apparatus attached to an animal.

FIG. 30 illustrates an actual experimental animal demonstrating the functionality of a version of the apparatus described in FIG. 26 following the deployment method described in FIG. 22 in which a percutaneously placed catheter delivers a sealed matrix containing electrodes onto the epicardium for heart contractility measurements. In this experiment, an anesthetized rat (40) was placed on a small animal ventilator (not shown) via a tracheostomy using a 16 gauge angiocathter placed into the trachea (41). A median sternotomy was performed to expose the heart (50). The heart contractility sensor containing the matrix-embedded electrodes (51) was then placed in direct contact with the epicardium (42). For this experiment, the matrix consisted of sodium polyacrylate hydrogel with Parafilm used to seal the hydrogel-surrounded electrodes. Through a puncture incision in the lateral chest wall (44) the connecting wires (45) were brought extracorporeally and connected to an impedance monitoring device (46).

Figure 31:
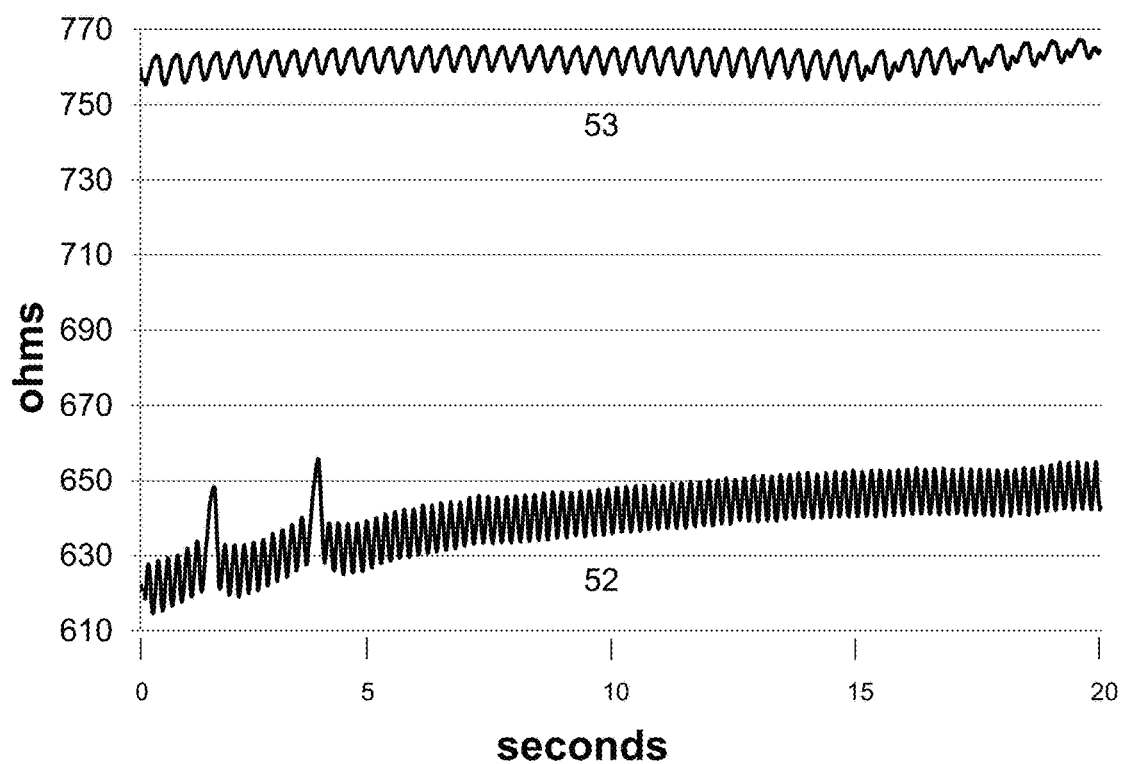
FIG. 31 depicts experimentally derived data from a small animal ventilator as shown in FIG. 30.

FIG. 31 demonstrates experimentally derived data from an experimental rat as illustrated in FIG. 30 under general anesthesia on a small animal ventilator with ventilations temporarily held for 20 seconds for cardiac contractility measurements. First, a baseline cardiac contractility curve was generated under normal cardiac filling pressures and a normal rat heart rate of approximately 309 beats per minute; the amplitude of the contractility cycle measured by the sensor was approximately 13 ohms and a sharp-pointed curve was observed suggesting preserved myocardial contractility (52). Without altering the positioning of the contractility sensor, the inferior vena cava of the same experimental animal was then clamped for 60 seconds to impede venous return to the heart to mimic the pathologic condition of hypovolemic shock. Under these conditions (curve indicated by 53) the amplitude of resistance change detected by the compliance measurement sensor was decreased to approximately 7 ohms, or slightly greater than one half the baseline amplitude (52). Additionally, bradycardia was noted with a heart rate reduced to approximately 141 beats per minute and a much more blunt-tipped curve was observed suggesting more sluggish myocardial movement consistent with compromised contractility (53). This demonstrates the ability of an epicardially placed contractility sensor to detect pathologic changes in the heart with a high degree of sensitivity; such a catheter could be placed in the pericardium routinely at the time of heart surgery or heart transplant to provide sensitive monitoring of the post-operative state of the heart or could be delivered via ultrasound-guided pericardiocentesis to monitor cardiac contractility changes in patients with heart failure.

Another embodiment of the matrix embedded electrodes pertains to surgical instruments with a sensitive tissue compressibility sensor at the instrument-tissue contact point to provide feedback about the contacted tissues that approaches the sensitivity of the tactile feedback of a surgeon's gloved hand. With conventional open surgery the tactile input of the surgeon's hand is vital to the precise identification and/or isolation of anatomic structures. In the case of tissue dissection, for example, undue mechanical resistance of the tissue to passage of the dissecting instrument as sensed by the surgeon's tactile input suggests that the dissecting instrument has entered an incorrect plane of dissection which can result in tissue injury. In the case of open heart procedures such as ablative procedures for atrial fibrillation performed at the time of valve replacement, the surgeon confirms adequate contact of the ablation catheter to the endocardial surface to achieve a satisfactory ablative lesion through tactile feedback of the mechanical resistance of the endocardial tissues to advancement of the ablative catheter. During open lung surgery, tumors within the lung parenchyma that are not visible to the naked eye can be precisely identified by the surgeon's palpation of a focus of firm tissue in a background of relatively deformable lung tissue. In endoscopic, endovascular, or robotic surgery, tactile input is compromised due to the inability of the surgeon to place hands on or near the tissues being dissected which results in a potentially greater risk of tissue injury, failure to achieve adequate contact of the surgical or endovascular instrument with target tissues, or failure to identify target lesions. A robotic, endoscopic, or endovascular instrument that included a sensor with sensitivity similar to the tactile sensitivity of the surgeon's hand could improve the safety and efficacy of robotic, endoscopic, or endovascular procedures requiring precise identification and/or isolation of anatomic structures.

Figure 32:
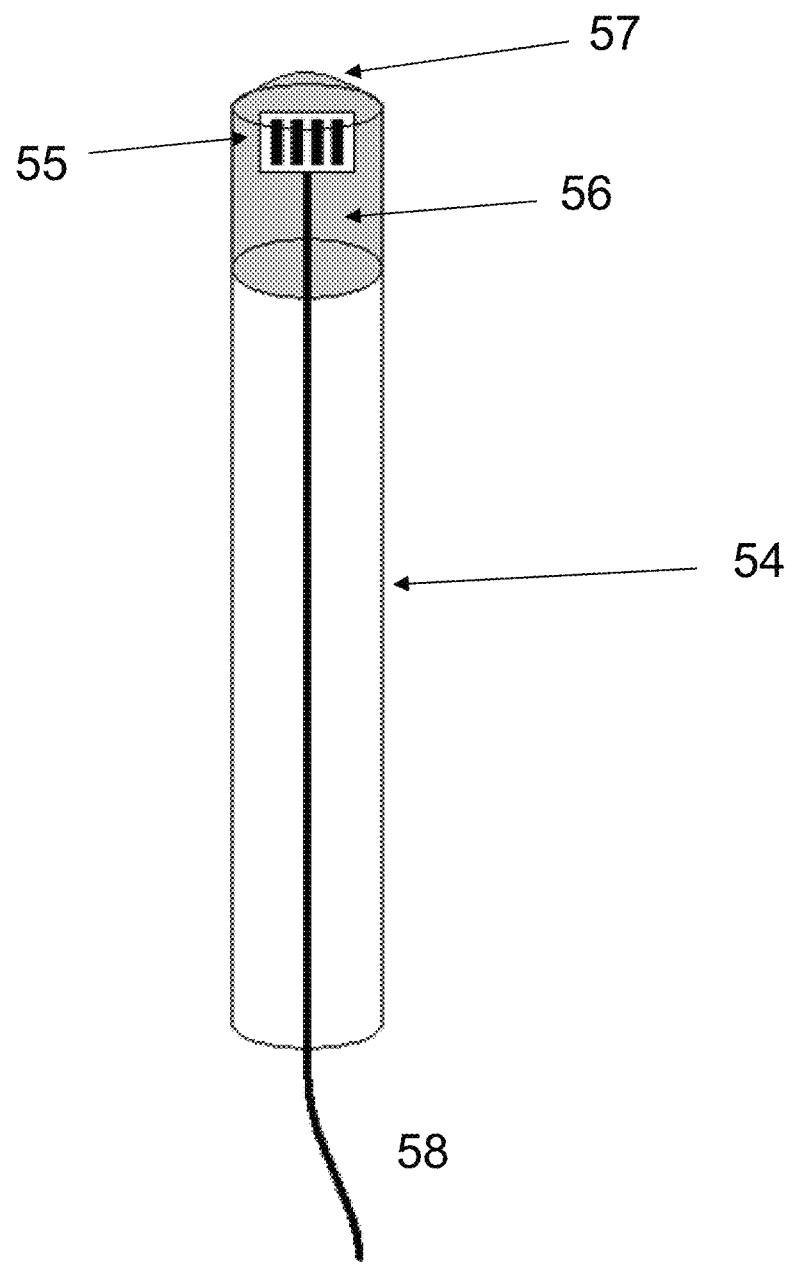
FIG. 32 depicts a tissue probe with matrix-embedded electrodes at the probe-tissue interface.

FIG. 32 illustrates a tissue probe with matrix-embedded electrodes at the probe-tissue interface. The body of the probe consisted of a rigid, thin-walled plastic housing (54) in which a four electrode array (55) was embedded in a matrix of sodium polyacrylate hydrogel (56) contained by a thin deformable membrane of Parafilm at the point of contact of the probe with the tissues (57). The electrodes were connected via wires (58) to an electrical resistance monitor (not shown). The detector was designed to sense pressure at the probe-tissue interface (57); if the probe were advanced into tissues with high mechanical resistance, the high pressure encountered at the probe-tissue interface would result in deformation of the membrane at the tip of the probe (57) and compression of the hydrogel matrix (56) resulting in a relatively large magnitude decrease in electrical impedance as sensed by the electrodes (55). If on the other hand the probe contacted tissue with relatively low mechanical resistance, no change or only a small magnitude drop in electrical impedance would be induced within the hydrogel matrix (56) as sensed by the electrodes (55).

Figure 33:
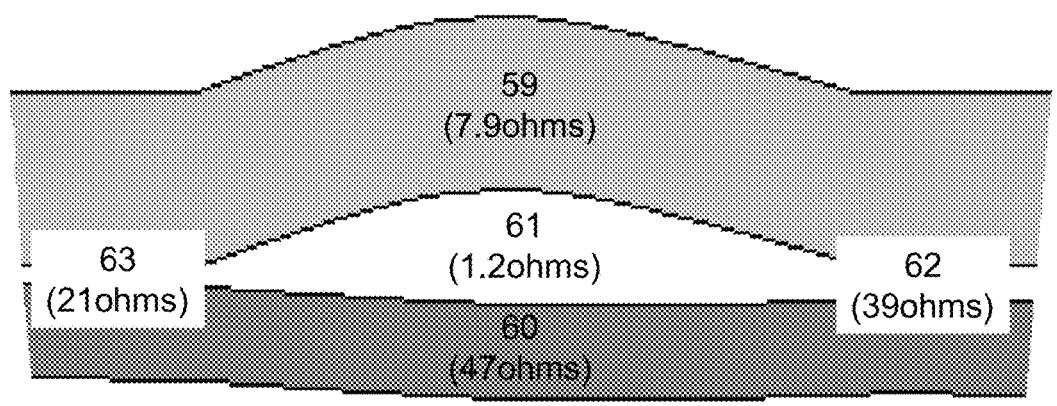
FIG. 33 depicts a schematic diagram of the difference between high and low resistance tissues.

FIG. 33 represents an actual experimental rat anatomic model that demonstrates the ability of the probe illustrated in FIG. 32 to distinguish between high and low mechanical-resistance tissues. The trachea (59) of an anesthetized experimental rat was dissected away from the esophagus (60) using a conventional dissector to establish a clear dissection plane free of tissues (61) to represent an area of minimal tissue mechanical resistance. Rostral (62) and caudal (63) to the dissection plane (61) the tracheoesophageal groove was left undissected to represent areas of very high tissue mechanical resistance. The probe of FIG. 32 was then advanced sequentially into each tissue region (59-63) and electrical impedance measurements were obtained to determine the mechanical resistance of the tissues in each region. In the dissected plane between the trachea and esophagus (61), only a very small change in impedance with advancement of the probe was observed (1.2 ohms), indicating very low mechanical resistance to passage and a very small deformation of the dissector tip in that tissue region. In three regions (60, 62, 63) a large impedance change was measured with advancement of the probe (47 ohms, 39 ohms, 21 ohms respectively) indicating that in these tissue regions the probe encountered high mechanical resistance of the tissues and a large deformation of the probe tip. An intermediate change in impedance was measured when the probe was advanced into the trachea (59, 7.9 ohms) because the softer tissues and complete dissection of the trachea made it more compliant to the advancement of the probe. This experiment demonstrates the ability of this embodiment of the invention to sensitively differentiate the mechanical properties of tissues at a small scale. This embodiment of the matrix-embedded electrodes could be used to guide dissection during endoscopic or robotic surgery or could be incorporated into a cardiac catheter to identify contact of the catheter with endocardial targets during interventional cardiology. It could also be used at the time of robotic lung surgery to identify the location of tumors lying within the lung parenchyma by contact of the probe with the lung surface due to the fact that lung tumors represent distinctly firm tissue compared to the relatively mechanically compliant surrounding lung parenchyma.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A physiological change monitoring system comprising:
    a saline-impregnated porous polymeric foam matrix, wherein the saline-impregnated porous polymeric foam matrix is configured to be positionable in an opening in a body during use, and wherein the saline-impregnated porous polymeric foam matrix comprises a saline solution absorbed within a porous polymeric foam matrix;
    a plurality of electrodes disposed in the saline-impregnated porous polymeric foam matrix;
    a resistance measuring device coupled to the electrodes, wherein the resistance measuring device determines a change in the resistance between at least two of the electrodes
    a container, the saline-impregnated porous polymeric foam matrix being positioned in the container; and
    a balloon positioned in the container, wherein inflation of the balloon compresses the saline-impregnated porous polymeric foam matrix.

2. The system of claim 1, wherein the saline-impregnated porous polymeric foam matrix is positionable proximate an organ.

3. The system of claim 1, wherein the saline leaves the saline-impregnated porous polymeric foam matrix during compression of the saline-impregnated porous polymeric foam matrix and the saline leaving the saline-impregnated porous polymeric foam matrix is contained by the container.

4. The system of claim 1, wherein the electrodes are positioned in the saline-impregnated porous polymeric foam matrix such that the distance between the electrodes changes as the saline-impregnated porous polymeric foam matrix is compressed or expanded.

5. The system of claim 1, wherein the electrodes are coupled to a substrate positioned within the saline-impregnated porous polymeric foam matrix.

6. The system of claim 1, wherein the saline-impregnated porous polymeric foam matrix is moldable.

7. The system of claim 1, wherein the saline-impregnated porous polymeric foam matrix has a shape that allows the saline-impregnated porous polymeric foam matrix to be disposed in a portion of a human esophagus.

8. The system of claim 1, wherein the saline-impregnated porous polymeric foam matrix has a shape that allows the saline-impregnated porous polymeric foam matrix to be disposed proximate to a portion of a lung.

9. The system of claim 1, wherein the saline-impregnated porous polymeric foam matrix has a shape that allows the saline-impregnated porous polymeric foam matrix to be disposed in a portion of a gastrointestinal tract.

10. The system of claim 1, wherein the saline-impregnated porous polymeric foam matrix has a shape that allows the saline-impregnated porous polymeric foam matrix to be disposed in a portion of a stomach.

11. The system of claim 1, wherein the saline-impregnated porous polymeric foam matrix has a shape that allows the saline-impregnated porous polymeric foam matrix to be disposed proximate to a portion of a heart.

12. A method of monitoring physiological changes in a body comprising:
    inserting a monitoring device in an opening of the body, wherein the monitoring device comprises:
        a saline-impregnated porous polymeric foam matrix, wherein the saline-impregnated porous polymeric foam matrix is configured to be positionable in an opening in a body during use, and wherein the saline-impregnated porous polymeric foam matrix comprises a saline solution absorbed within a porous polymeric foam matrix;
        a plurality of electrodes disposed in the saline-impregnated porous polymeric foam matrix; and
        a resistance measuring device coupled to the electrodes, wherein the resistance measuring device determines a change in the resistance between at least two of the electrodes;
    adjusting the baseline resistance between at least two of the electrodes by altering the amount of saline in the saline-impregnated porous polymeric foam matrix by removing saline from the foam using a suction catheter; and
    monitoring the resistance between two or more of the electrodes.

* * * * *